(12) United States Patent
Penner et al.

(10) Patent No.: US 7,906,709 B2
(45) Date of Patent: Mar. 15, 2011

(54) METHODS FOR BREEDING GLYPHOSATE RESISTANT PLANTS AND COMPOSITIONS THEREOF

(75) Inventors: Donald Penner, Williamston, MI (US); Marulak Simarmata, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1033 days.

(21) Appl. No.: 11/656,817

(22) Filed: Jan. 23, 2007

(65) Prior Publication Data
US 2007/0180574 A1 Aug. 2, 2007

Related U.S. Application Data

(60) Provisional application No. 60/761,216, filed on Jan. 23, 2006, provisional application No. 60/761,710, filed on Jan. 23, 2006.

(51) Int. Cl.
*A01H 5/00* (2006.01)
*A01H 5/10* (2006.01)
(52) U.S. Cl. ........................................ 800/300; 800/298
(58) Field of Classification Search .................. None
See application file for complete search history.

(56) References Cited

U.S. PATENT DOCUMENTS

| | | | |
|---|---|---|---|
| 4,499,687 A | 2/1985 | Lawrence, Jr. et al. | |
| 4,535,060 A | 8/1985 | Comai | |
| 4,751,347 A | 6/1988 | Erickson | |
| 4,769,061 A | 9/1988 | Comai | |
| 4,940,835 A | 7/1990 | Shah et al. | |
| 4,971,908 A | 11/1990 | Kishore et al. | |
| 5,094,945 A | 3/1992 | Comai | |
| 5,145,783 A | 9/1992 | Kishore et al. | |
| 5,188,642 A | 2/1993 | Shah et al. | |
| 5,310,667 A | 5/1994 | Eichholtz et al. | |
| 5,312,910 A | 5/1994 | Kishore et al. | |
| 5,352,605 A | 10/1994 | Fraley et al. | |
| 5,384,253 A | 1/1995 | Krzyzek et al. | |
| 5,463,175 A | 10/1995 | Barry et al. | |
| 5,530,196 A | 6/1996 | Fraley et al. | |
| 5,554,798 A | 9/1996 | Lundquist et al. | |
| 5,585,742 A | 12/1996 | Kamiya | |
| 5,627,061 A | 5/1997 | Barry et al. | |
| 5,633,435 A | 5/1997 | Barry et al. | |
| 5,792,930 A | 8/1998 | Chaubet et al. | |
| 5,804,425 A | 9/1998 | Barry et al. | |
| 5,981,832 A | 11/1999 | Johnson | |
| 6,040,497 A | 3/2000 | Spencer et al. | |
| 6,066,786 A | 5/2000 | Rose-Fricker | |
| 6,204,436 B1 | 3/2001 | Mannerloef et al. | |
| 6,225,114 B1 | 5/2001 | Eichholtz et al. | |
| 6,303,848 B1 | 10/2001 | Kumagai et al. | |
| 6,362,396 B1 | 3/2002 | Chaubet et al. | |
| 6,423,887 B1 | 7/2002 | Rose-Fricker | |
| 6,426,185 B1 | 7/2002 | Kumagai et al. | |
| 6,566,587 B1 | 5/2003 | Lebrun et al. | |
| 6,613,963 B1 | 9/2003 | Gingera et al. | |
| 6,750,377 B1 | 6/2004 | Kaster, Jr. et al. | |
| 6,762,344 B1 | 7/2004 | Spencer et al. | |
| 6,803,501 B2 * | 10/2004 | Baerson et al. | 800/300 |
| 6,825,400 B2 | 11/2004 | Behr et al. | |
| 6,867,293 B2 | 3/2005 | Andrews et al. | |
| 6,870,075 B1 | 3/2005 | Beetham et al. | |
| 6,927,319 B2 | 8/2005 | Davis | |
| 7,465,857 B1 | 12/2008 | van 't Klooster | |
| 2003/0192072 A1 | 10/2003 | Baerson et al. | |
| 2004/0148650 A1 | 7/2004 | Baerson et al. | |
| 2005/0108786 A1 | 5/2005 | Heck et al. | |
| 2005/0188434 A1 | 8/2005 | Spencer et al. | |

FOREIGN PATENT DOCUMENTS

| | | |
|---|---|---|
| EP | 0189707 | 8/1986 |
| EP | 0218571 | 4/1987 |
| EP | 0508909 | 10/1992 |
| EP | 0924299 | 6/1999 |
| GB | 2 326 163 | * 12/1998 |
| WO | WO 92/00377 | 1/1992 |
| WO | WO 92/04449 | 3/1992 |

OTHER PUBLICATIONS

Baerson et al 2002 Weed Science 50: 721-730.*
Jones et al 2001 Theoretical and Applied Genetics 102: 405-415.*
Baerson et al., Glyphosate-Resistant Goosegrass. Identification of a Mutation in the Target Enzyme 5-Enolpyruvylshikimate-3-Phosphate Sunthase, Plant Physiol. 129:1265-1275 (2002).
Baerson et al., Investigating the mechanism of glyphosate resistance in rigid ryegrass (*Lolium ridigum*), Weed Sci. 50:721-730 (2002).
Boerboom et al., Mechanism of Glyphosate Tolerance in Birdsfoot Trefoil (*Lotus corniculatus*), Weed Sci. 38:463-467 (1990).
Bradshaw et al., Perspectives on Glyphosate Resistance, Weed Technology 11:189-198 (1997).
Brown et al., Twists and turns: a tale of two shikimate-pathyway enzymes, Biochem. Soc. Trans. 31:543-547 (2003).
Chomczynski et al, Single-Step Method of RNA Isolation by Acid Guanidinium Thiocyanate-Phenol-Chloroform Extraction, Anal. Biochem. 162:156-159 (1987).
Clapp, Somatic Gene Therapy Into Hematopoietic Cells—Current Status and Future Implications, Clin. Perinatol. 20(1):155-168 (1993).
Coruzzi et al., Tissue-specific and light-regulated expression of a pea nuclear gene encoding the small subunit of ribulose-1,5-bisphosphate carboxylase, EMBO J. 3(8):1671-1679 (1984).

(Continued)

Primary Examiner — David H Kruse
(74) Attorney, Agent, or Firm — Harness, Dickey & Pierce, P.L.C.

(57) ABSTRACT

A plant comprising SEQ. ID. NO.2 or a functional portion thereof, wherein SEQ ID. NO. 2 is not native to said plant. A glyphosate resistant grass of economic value comprises a nucleic acid molecule that encodes an EPSPS enzyme. In some embodiments, the nucleic acid molecule comprises a sequence of SEQ. ID. NO. 1, or a functional portion thereof. In some embodiments, the EPSPS enzyme can be a polypeptide molecule comprising an amino acid sequence that is essentially of SEQ. ID. NO. 2, or portion thereof. Embodiments include a DNA construct comprising a SEQ. ID. NO. 1 or a functional portion thereof and transgenic methods for inserting the DNA construct into a plant. Some embodiments include non-transgenic glyphosate resistant turfgrasses.

11 Claims, 5 Drawing Sheets

OTHER PUBLICATIONS

Coupland, The Effect of Temperature on the Activity and Metabolism of Glyphosate Applied to Rhizome Fragments of *Elymus repens* (=Agropyronrepens), Pestic. Sci. 15:226-234 (1985).

della-Cioppa et al., Translocation of the precursor of 5-enolpyruvylshikimate-3-phosphate synthase into chloroplasts of higher plants in vitro, Proc. Natl. Acad. Sci. 83:6873-6877 (1986).

Diggle et al., The Population Dynamics and Genetics of Herbicide Resistance—A Modeling Approach, Herbicide Resistance and World Grains, 61-99 (2001).

Don et al., 'Touchdown' PCR to circumvent spurious priming during gene amplification, Nucl. Acids Res. 19(14):4008 (1991).

Emanuelsson et al., ChloroP, a neutral network-based method for predicting chloroplast transit peptides and their cleavage sites, Protein Sci. 8:978-984 (1999).

Felsot, Herbicide Tolerant Genes, Part 1: Squaring Up Roundup Ready Crops, Agrichemical and Environmental News, 1-12 (2000).

Feng et al., Resistance to glyphosate in *Lolium rigidum*. II. Uptake, translocation, and metabolism, Weed Sci. 47:412-415 (1999).

Fraley et al., Expression of bacterial genes in plant cells, Proc. Natl. Acad. Sci. 80:4803-4807 (1983).

Fromm et al., Expression of genes transferred into monocot and dicot plant cells by electroporation, Proc. Natl. Acad. Sci. 82:5824-5828 (1985).

Gasser et al., Structure, Expression, and Evolution of the 5-Enolpyruvylshikimate-3-phosphate Synthase Genes Petunia and Tomato, J. Biol. Chem. 263(9):4280-4289 (1988).

GenBank Accession No. AF349754, *Lolium rigidum* 5-enolpyruvylshikimate 3-phosphate synthase (epsp-s) mRNA, epsp-s-S allele, partcial cds (Jan. 2003).

GenBank Accession No. AJ310166, *Lolium rigidum* mRNA for 5-enol-pyruvylshikimate-3-phosphate synthase homologue (Jan. 2004).

GenBank Accession No. DQ153168, *Lolium multiflorum* plastid 5-enolpyruvylshikimate 3-phosphate synthase mRNA, partial cds; nuclear gene for plastid product (Aug. 2006).

GenBank Accession No. DQ303395, *Lolium rigidum* biotype VLR 1 5-enolpyruvylshikimate 3-phosphate synthase (EPSPS) mRNA, EPSPS-S allele, partial cds, (Sep. 2006).

GenBank Accession No. DQ303396, *Lolium rigidum* biotype VLR 15 5-enolpyruvylshikimate 3-phosphate synthase (EPSPS) mRNA, EPSPS-S allele, partial cds, (Sep. 2006).

GenBank Accession No. DQ303397, *Lolium rigidum* biotype NLR 70 5-enolpyruvylshikimate 3-phosphate synthase (EPSPS) mRNA, EPSPS-S allele, partial cds, (Sep. 2006).

GenBank Accession No. DQ303398, *Lolium rigidum* biotype NLR 71 5-enolpyruvylshikimate 3-phosphate synthase (EPSPS) mRNA, EPSPS-S allele, partial cds, (Sep. 2006).

GenBank Accession No. DQ303399, *Lolium rigidum* biotype NLR 72 5-enolpyruvylshikimate 3-phosphate synthase (EPSPS) mRNA, EPSPS-S allele, partial cds, (Sep. 2006).

GenBank Accession No. DQ303400, *Lolium rigidum* biotype NLR 75 5-enolpyruvylshikimate 3-phosphate synthase (EPSPS) mRNA, EPSPS-S allele, partial cds, (Sep. 2006).

GenBank Accession No. DQ303401, *Lolium rigidum* biotype NLR 76 5-enolpyruvylshikimate 3-phosphate synthase (EPSPS) mRNA, EPSPS-S allele, partial cds, (Sep. 2006).

GenBank Accession No. DQ303402, *Lolium rigidum* biotype NLR 79 5-enolpyruvylshikimate 3-phosphate synthase (EPSPS) mRNA, EPSPS-S allele, partial cds, (Sep. 2006).

GenBank Accession No. DQ303403, *Lolium rigidum* biotype NLR 84 5-enolpyruvylshikimate 3-phosphate synthase (EPSPS) mRNA, EPSPS-S allele, partial cds, (Sep. 2006).

GenBank Accession No. DQ303404, *Lolium rigidum* biotype SLR 76 5-enolpyruvylshikimate 3-phosphate synthase (EPSPS) mRNA, EPSPS-S allele, partial cds, (Sep. 2006).

GenBank Accession No. DQ303405, *Lolium rigidum* biotype SLR 77 5-enolpyruvylshikimate 3-phosphate synthase (EPSPS) mRNA, EPSPS-S allele, partial cds, (Sep. 2006).

Gepts, A Comparison between Crop Domestication, Classical Plant Breeding, and Genetic Engineering, Crop Sci. 42:1780-1790 (2002).

Graham et al., Transformation of Rat Cells by DNA of Human Adenovirus 5, Virology 54:536-539 (1973).

Heap, *Lolium rigidum*—Rigid ryegrass, International Survey of Herbicide-Resistant Weeds, http://www.weedscience.com (2004).

Johnston et al., Gene Gun Transfection of Animal Cells and Genetic Immunization, Methods Cell Biol. 43:353-365 (1994).

Kishore et al., Amino Acid Biosynthesis Inhibitors as Herbicides, Annu. Rev. Biochem. 57:627-663 (1988).

Kishore et al., 5-Enolpyruvylshikimate 3-Phosphate Synthase: From Biochemistry to Genetic Engineering of Glyphosate Tolerance, Biotechnology for Crop Protection, ACS Symposium Series No. 379:37-48 (1988).

Klee et al., Cloning of an *Arabidopsis thaliana* gene encoding 5-enolpyruvylshikimate-3-phosphate synthase: sequence analysis and manipulation to obtain glyphosate-tolerant plants, Mol. Gen. Genet. 210:437-442 (1987).

Lee et al., Examining the possibility of a two-gene system conferring glyphosate resistance, Abstract from 2006 Meeting of the Weed Science Society of America, vol. 46 (2006).

Lee et al., Influence of formulated glyphosate and activator adjuvants on *Sclerotinia sclerotiorum* in glyphosate-resistant and -susceptible *Glycine max*, Weed Science 48:710-715 (2000).

Levett et al., Identification of domains responsible for signal recognition and transduction within the QUTR transcription repressor protein, Biochem. J. 350:189-197 (2000).

Lorraine-Colwill et al., Inheritance of evolved glyphosate resistance in *Lolium rigidum* (Gaud.), Theor. Appl. Genet. 102:545-550 (2001).

Lorraine-Colwill et al., Resistance to glyphosate in *Lolium rigidum*, Pestic. Sci. 55:486-503 (1999).

Padgette et al., Site-directed Mutagenesis of a Conserved Region of the 5-Enolpyruvylshikimate-3-phospate Synthase Active Site, J. Biol. Chem. 266(33):22364-22369 (1991).

Perez-Jones et al., Identification of glyphosate-resistant Italian ryegrass (*Lolium multiflorum*) in Oregon, Weed Science 53:775-779 (2005).

Simarmata et al., Inheritance of glyphosate resistance in rigid ryegrass (*Lolium rigidum*) from California, Weed Science 53:615-619 (2005).

Simarmata et al., Potential basis of glyphosate resistance in California rigid ryegrass (*Lolium rigidum*), Weed Science 51:678-682 (2003).

Wakelin et al., Glyphosate resistance in four different populations of *Lolium rigidum* is associated with reduced translocation of glyphosate to meristematic zones, Weed Research 44:453-459 (2004).

Wakelin, A target-site mutation is present in a glyphosate-resistant *Lolium rigidum* population, Weed Research 46:432-440 (2006).

Lu et al., High Efficiency Retroviral Mediated Gene Transduction into Single Isolated Immature and Replatable CD343+ Hematopoietic Stem/Progenitor Cells from Human Umbilical Cord Blood, J. Exp. Med. 178:2089-2096 (1993).

Matteucci et al., Synthesis of Deoxyoligonucleotides on a Polymer Support, J. Am. Chem. Soc. 103:3185-3191 (1981).

Nair, Developing tetraploid perennial ryegrass (*Lolium perenne* L.) populations, New Zealand Journal of Agricultural Research, 47:45-49 (2004).

Odell et al., Identification of DNA sequences required for activity of the cauliflower mosaic virus 35S promoter, Nature 313:810-812 (1985).

Owen et al., Herbicide-resistant crops and weed resistance to herbicides, Pest Manag. Sci. 61:301-311 (2005).

Pereira et al., Structural bioinformatics study of EPSP synthase from *Mycobacterium tuberculosis*, Biochem. and Biophys. Research Communications 312:608-614 (2003).

Peters et al., A Modular Vector for *Agrobacterium* Mediated Transformation of Wheat, Plant Molecular Biology Reporter 17:323-331 (1999).

Pratley et al., Resistance to glyphosate in *Lolium rigidum*. I. Bioevaluation, Weed Science 47:405-411 (1999).

Sandberg et al., Absorption, translocation and metabolism of 14C-glyphosate in several weed species, Weed Res. 20:195-200 (1980).

Schein et al., Chloroplast transit peptide prediction: a peek inside the black box, Nucl. Acids Res. 29(16):1-6 (2001).

Schibeci et al., Isolation of plasma membrane from protoplasts of *Lolium multiflorum* (ryegrass) endosperm cells, Biochem. J. 205:511-519 (1982).

Schuler et al., Structural sequences are conserved in the genes coding for the α, α' and β-subunits of the soybean 7S seed storage protein, Nuc. Acids Res. 10(24):8245-8261 (1982).

Schulz et al., Insensitivity of 5-enolphyruvylshikimic acid-3-phosphate synthase to glyphosate confers resistance to this herbicide in a strain of Aerobacter aerogenes, Arch. Microbiol. 137:121-123 (1984).

Shah et al., Engineering Herbicide Tolerance in Transgenic Plants, Science 233:478-481 (1986).

Sost et al., Characterization of a glyphosate-insensitive 5-enolpyruvylshikimic acid-3-phosphate synthase, FEBS Lett. 173(1):238-242 (1984).

Stallings et al., Structure and topological symmetry of the glyphosate target 5-enol-pyruvylshikimate-3-phosphate synthase: A distinctive protein fold, Proc. Natl. Acad. Sci. 88:5046-5050 (1991).

Sun et al., Novel AroA with High Tolerance to Glyphosate, Encoded by a Gene of *Pseudomonas putida* 4G-1 Isolated from an Extremely Polluted Environment in China, Applied and Environmental Microbiology 71(8):4771-4776 (2005).

Van Heeswijck et al., The role of biotechnology in perennial grass improvement for temperate pastures, New Zealand Journal of Agricultural Research 37:427-438 (1994).

Wagner et al., Coupling of adenovirus to transferrin-polylysine/DNA complexes greatly enhances receptor-mediated gene delivery and expression of transfected genes, Proc. Natl. Acad. Sci. 89:6099-6103 (1992).

Westwood et al., Cellular mechanisms influence differential glyphosate sensitivity in field bindweed (*Convolvulus arvensis*) biotypes, Weed Sci. 45:2-11 (1997).

Wong et al., Electric Field Mediated Gene Transfer, Biochem. Biophys. Res. Commun. 107(2):584-587 (1982).

Zhou et al., Glyphosate-tolerant CP4 and GOX genes as a selectable marker in wheat transformation, Plant Cell Rep. 15:159-163 (1995).

* cited by examiner

*Primer Abreviation:*

| | |
|---|---|
| FP1 | : 5'-GAT GCC AAG GAG GAA GTA AAG-3' |
| FP2 | : 5'-TGC TAT CAG AGA TGT TGC GTC CTG-3' |
| RP1 | : 5'-TCT CTG GTG GCG TGA TAA TG-3' |
| RP2 | : 5'-AAC AGG TGG GCA GTC AGT G-3' |
| RP3 | : 5'-ATA GGA CGC TCC CTC ATT CTT GGT-3' |
| RP4 | : 5'-TTT CCA CCA GCA GCT ACT ACA GCA-3' |
| dT-anchor | : 5'-GAC CAC GCG TAT CGA TGT CGA CTT TTT TTT TTT-3' |
| Anchor Primer | : 5'-GAC CAC GCG TAT CGA TGT CGA C-3' |

SEQUENCE LISTING

```
<160> NUMBER OF SEQ ID NOS: 18

<210> SEQ ID NO 1
<211> LENGTH: 1320
<212> TYPE: DNA
<213> ORGANISM: Lolium rigidum
<220> FEATURE:
<221> NAME/KEY: CDS
<222> LOCATION: (1)..(1320)
<223> OTHER INFORMATION: Resistant (R) biotype

<400> SEQUENCE: 1 gtg ctg cag ccc atc aag gag atc tcc ggc gcc gtg cag ctg ccc ggc      48
Val Leu Gln Pro Ile Lys Glu Ile Ser Gly Ala Val Gln Leu Pro Gly
1               5                   10                  15 tcc aag tcg ctc tcc aac cgg atc cta ctc ctc tcc gcc ttg tcc gag      96
Ser Lys Ser Leu Ser Asn Arg Ile Leu Leu Leu Ser Ala Leu Ser Glu
                20                  25                  30 gga aca act gtc gtg gat aac ctg ttg aac agc gag gat gtg cac tac     144
Gly Thr Thr Val Val Asp Asn Leu Leu Asn Ser Glu Asp Val His Tyr
            35                  40                  45
```

```
atg ctc gag gcc ctg gac gcg ctc ggg ctc tcc gtg gaa gca gac aaa    192
Met Leu Glu Ala Leu Asp Ala Leu Gly Leu Ser Val Glu Ala Asp Lys
     50                  55                  60 gtt gca aaa aga gct gta gtc gtt ggc tgt ggc ggc agg ttc ccg att    240
Val Ala Lys Arg Ala Val Val Val Gly Cys Gly Gly Arg Phe Pro Ile
 65                  70                  75                  80 gaa aag gat gcc aaa gag gaa gta aag ctc ttc ttg ggg aac gct gga    288
Glu Lys Asp Ala Lys Glu Glu Val Lys Leu Phe Leu Gly Asn Ala Gly
                 85                  90                  95 act gcg atg cgg tca ttg acg gca gca gta gta gct gct ggt gga aat    336
Thr Ala Met Arg Ser Leu Thr Ala Ala Val Val Ala Ala Gly Gly Asn
            100                 105                 110 gca act tat gtt ctt gat gga gta cca aga atg agg gag cga cct atc    384
Ala Thr Tyr Val Leu Asp Gly Val Pro Arg Met Arg Glu Arg Pro Ile
        115                 120                 125 ggt gac tta gtt gtc ggt ttg aaa caa cta ggt gcg aat gtt gat tgt    432
Gly Asp Leu Val Val Gly Leu Lys Gln Leu Gly Ala Asn Val Asp Cys
130                 135                 140 ttc ctc ggc act gac tgc cca cct gtt cgt atc aat ggc att gga ggg    480
Phe Leu Gly Thr Asp Cys Pro Pro Val Arg Ile Asn Gly Ile Gly Gly
145                 150                 155                 160 cta cct ggt ggc aag gtt aag ctg tct ggt tcc atc agc agc caa tac    528
Leu Pro Gly Gly Lys Val Lys Leu Ser Gly Ser Ile Ser Ser Gln Tyr
                165                 170                 175 ttg agt tcc ttg ctg atg gct gct cct ttg gct ctt ggg gat gtc gag    576
Leu Ser Ser Leu Leu Met Ala Ala Pro Leu Ala Leu Gly Asp Val Glu
            180                 185                 190 att gaa atc att gat aaa cta atc tct gtt cct tac gtt gaa atg aca    624
Ile Glu Ile Ile Asp Lys Leu Ile Ser Val Pro Tyr Val Glu Met Thr
        195                 200                 205 ttg aga ttg atg gag cgt ttt ggc gtg acg gca gag cat tct gat agc    672
Leu Arg Leu Met Glu Arg Phe Gly Val Thr Ala Glu His Ser Asp Ser
210                 215                 220 tgg gac aga ttc tac att aaa gga gga cag aag tac aag tcc cct gga    720
Trp Asp Arg Phe Tyr Ile Lys Gly Gly Gln Lys Tyr Lys Ser Pro Gly
225                 230                 235                 240 aat gcc tat gtc gaa ggt gat gcc tcg agt gcg agt tat ttc ttg gct    768
Asn Ala Tyr Val Glu Gly Asp Ala Ser Ser Ala Ser Tyr Phe Leu Ala
                245                 250                 255 ggt gct gca atc act gga gga act gtg act gtc caa ggt tgc ggc acc    816
Gly Ala Ala Ile Thr Gly Gly Thr Val Thr Val Gln Gly Cys Gly Thr
            260                 265                 270 acc agt ttg cag ggt gat gtg aaa ttt gct gag gta cta gaa atg atg    864
Thr Ser Leu Gln Gly Asp Val Lys Phe Ala Glu Val Leu Glu Met Met
        275                 280                 285 gga gcg aag gtt aca tgg act gac act agt gta act gtt act ggt cca    912
Gly Ala Lys Val Thr Trp Thr Asp Thr Ser Val Thr Val Thr Gly Pro
290                 295                 300 ccg cgt cag ccc ttt gga agg aaa cac ctg aaa gct gtt gat gtc aac    960
Pro Arg Gln Pro Phe Gly Arg Lys His Leu Lys Ala Val Asp Val Asn
305                 310                 315                 320 atg aac aaa atg cct gat gtt gcc atg act ctt gcc gtt gtt gcc ctt    1008
Met Asn Lys Met Pro Asp Val Ala Met Thr Leu Ala Val Val Ala Leu
                325                 330                 335 ttt gcc gat ggt cca act gct atc aga gat gtt gcc tcc tgg aga gtg    1056
Phe Ala Asp Gly Pro Thr Ala Ile Arg Asp Val Ala Ser Trp Arg Val
            340                 345                 350 aag gaa acc gag aga atg gtg gca atc tgc acg gaa cta aca aag ctg    1104
Lys Glu Thr Glu Arg Met Val Ala Ile Cys Thr Glu Leu Thr Lys Leu
        355                 360                 365
```

```
gga gca acg gta gag gaa ggc ccg gac tac tgc att atc aca cca cca    1152
Gly Ala Thr Val Glu Glu Gly Pro Asp Tyr Cys Ile Ile Thr Pro Pro
    370                 375                 380 gag aag ctg aac gtc acg gca atc gac acc tac gat gac cac cgg atg    1200
Glu Lys Leu Asn Val Thr Ala Ile Asp Thr Tyr Asp Asp His Arg Met
385                 390                 395                 400 gcg atg gcc ttc tcc ctc gcc gcc tgc gct gag gtg cct gtc acg atc    1248
Ala Met Ala Phe Ser Leu Ala Ala Cys Ala Glu Val Pro Val Thr Ile
                405                 410                 415 agg gac cct ggg tgc acc cgc aag acc ttc ccc aac tac ttt gac gtg    1296
Arg Asp Pro Gly Cys Thr Arg Lys Thr Phe Pro Asn Tyr Phe Asp Val
            420                 425                 430 cta agc acc tta gtg aag aac tag                                    1320
Leu Ser Thr Leu Val Lys Asn
            435

<210> SEQ ID NO 2
<211> LENGTH: 439
<212> TYPE: PRT
<213> ORGANISM: Lolium rigidum

<400> SEQUENCE: 2

Val Leu Gln Pro Ile Lys Glu Ile Ser Gly Ala Val Gln Leu Pro Gly
1

-continued

```
                275                 280                 285
Gly Ala Lys Val Thr Trp Thr Asp Thr Ser Val Thr Val Gly Pro
        290                 295                 300
Pro Arg Gln Pro Phe Gly Arg Lys His Leu Lys Ala Val Asp Val Asn
305                 310                 315                 320
Met Asn Lys Met Pro Asp Val Ala Met Thr Leu Ala Val Val Ala Leu
                325                 330                 335
Phe Ala Asp Gly Pro Thr Ala Ile Arg Asp Val Ala Ser Trp Arg Val
                340                 345                 350
Lys Glu Thr Glu Arg Met Val Ala Ile Cys Thr Glu Leu Thr Lys Leu
            355                 360                 365
Gly Ala Thr Val Glu Glu Gly Pro Asp Tyr Cys Ile Ile Thr Pro Pro
        370                 375                 380
Glu Lys Leu Asn Val Thr Ala Ile Asp Thr Tyr Asp Asp His Arg Met
385                 390                 395                 400
Ala Met Ala Phe Ser Leu Ala Ala Cys Ala Glu Val Pro Val Thr Ile
                405                 410                 415
Arg Asp Pro Gly Cys Thr Arg Lys Thr Phe Pro Asn Tyr Phe Asp Val
                420                 425                 430
Leu Ser Thr Leu Val Lys Asn
        435

<210> SEQ ID NO 3
<211> LENGTH: 21
<212> TYPE: DNA
<213> ORGANISM: Artificial Sequence
<220> FEATURE:
<223> OTHER INFORMATION: Synthetically derived primer

<400> SEQUENCE: 3
gatgccaagg aggaagtaaa g                                              21

<210> SEQ ID NO 4
<211> LENGTH: 24
<212> TYPE: DNA
<213> ORGANISM: Artificial Sequence
<220> FEATURE:
<223> OTHER INFORMATION: Synthetically derived primer

<400> SEQUENCE: 4
tgctatcaga gatgttgcgt cctg                                           24

<210> SEQ ID NO 5
<211> LENGTH: 24
<212> TYPE: DNA
<213> ORGANISM: Artificial Sequence
<220> FEATURE:
<223> OTHER INFORMATION: Synthetically derived primer

<400> SEQUENCE: 5
tgctatcaga gatgttgcgt cctg                                           24

<210> SEQ ID NO 6
<211> LENGTH: 19
<212> TYPE: DNA
<213> ORGANISM: Artificial Sequence
<220> FEATURE:
<223> OTHER INFORMATION: Synthetically derived primer

<400> SEQUENCE: 6
aacaggtggg cagtcagtg                                                 19
```

```
<210> SEQ ID NO 7
<211> LENGTH: 24
<212> TYPE: DNA
<213> ORGANISM: Artificial Sequence
<220> FEATURE:
<223> OTHER INFORMATION: Synthetically derived primer

<400> SEQUENCE: 7
ataggacgct ccctcattct tggt                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetically derived primer

<400> SEQUENCE: 8
tttccaccag cagctactac agca                                          24

<210> SEQ ID NO 9
<211> LENGTH: 33
<212> TYPE: DNA
<213> ORGANISM: Artificial Sequence
<220> FEATURE:
<223> OTHER INFORMATION: Synthetically derived primer

<400> SEQUENCE: 9
gaccacgcgt atcgatgtcg acttttttttt ttt                               33

<210> SEQ ID NO 10
<211> LENGTH: 22
<212> TYPE: DNA
<213> ORGANISM: Artificial Sequence
<220> FEATURE:
<223> OTHER INFORMATION: Synthetically derived primer

<400> SEQUENCE: 10
gaccacgcgt atcgatgtcg ac                                            22

<210> SEQ ID NO 11
<211> LENGTH: 18
<212> TYPE: DNA
<213> ORGANISM: Artificial
<220> FEATURE:
<223> OTHER INFORMATION: forward primer sequence for SNP assay

<400> SEQUENCE: 11
cggcaggttc ccgattga                                                 18

<210> SEQ ID NO 12
<211> LENGTH: 22
<212> TYPE: DNA
<213> ORGANISM: Artificial
<220> FEATURE:
<223> OTHER INFORMATION: reverse primer sequence for SNP assay

<400> SEQUENCE: 12
gcatttccac cagcagctac ta                                            22

<210> SEQ ID NO 13
<211> LENGTH: 16
<212> TYPE: DNA
<213> ORGANISM: Artificial
<220> FEATURE:
<223> OTHER INFORMATION: VIC labeled probe sequence for SNP assay
```

-continued

<400> SEQUENCE: 13
ccgtcaatgg ccgcat                                                           16

<210> SEQ ID NO 14
<211> LENGTH: 16
<212> TYPE: DNA
<213> ORGANISM: Artificial
<220> FEATURE:
<223> OTHER INFORMATION: FAM labeled probe sequence for SNP assay

<400> SEQUENCE: 14
ccgtcaatga ccgcat                                                           16

<210> SEQ ID NO 15
<211> LENGTH: 1176
<212> TYPE: DNA
<213> ORGANISM: Lolium rigidum
<220> FEATURE:
<221> NAME/KEY: CDS
<222> LOCATION: (1)..(1173)
<223> OTHER INFORMATION: Resistant (R) biotype

<400> SEQUENCE: 15

| | | |
|---|---|---|
| atg ctc gag gcc ctg gac gcg ctc ggg ctc tcc gtg gaa gca gac aaa<br>Met Leu Glu Ala Leu Asp Ala Leu Gly Leu Ser Val Glu Ala Asp Lys<br>1               5                   10                  15 | 48 |
| gtt gca aaa aga gct gta gtc gtt ggc tgt ggc ggc agg ttc ccg att<br>Val Ala Lys Arg Ala Val Val Val Gly Cys Gly Gly Arg Phe Pro Ile<br>            20                  25                  30 | 96 |
| gaa aag gat gcc aaa gag gaa gta aag ctc ttc ttg ggg aac gct gga<br>Glu Lys Asp Ala Lys Glu Glu Val Lys Leu Phe Leu Gly Asn Ala Gly<br>        35                  40                  45 | 144 |
| act gcg atg cgg tca ttg acg gca gca gta gta gct gct ggt gga aat<br>Thr Ala Met Arg Ser Leu Thr Ala Ala Val Val Ala Ala Gly Gly Asn<br>    50                  55                  60 | 192 |
| gca act tat gtt ctt gat gga gta cca aga atg agg gag cga cct atc<br>Ala Thr Tyr Val Leu Asp Gly Val Pro Arg Met Arg Glu Arg Pro Ile<br>65                  70                  75                  80 | 240 |
| ggt gac tta gtt gtc ggt ttg aaa caa cta ggt gcg aat gtt gat tgt<br>Gly Asp Leu Val Val Gly Leu Lys Gln Leu Gly Ala Asn Val Asp Cys<br>                85                  90                  95 | 288 |
| ttc ctc ggc act gac tgc cca cct gtt cgt atc aat ggc att gga ggg<br>Phe Leu Gly Thr Asp Cys Pro Pro Val Arg Ile Asn Gly Ile Gly Gly<br>            100                 105                 110 | 336 |
| cta cct ggt ggc aag gtt aag ctg tct ggt tcc atc agc agc caa tac<br>Leu Pro Gly Gly Lys Val Lys Leu Ser Gly Ser Ile Ser Ser Gln Tyr<br>        115                 120                 125 | 384 |
| ttg agt tcc ttg ctg atg gct gct cct ttg gct ctt ggg gat gtc gag<br>Leu Ser Ser Leu Leu Met Ala Ala Pro Leu Ala Leu Gly Asp Val Glu<br>    130                 135                 140 | 432 |
| att gaa atc att gat aaa cta atc tct gtt cct tac gtt gaa atg aca<br>Ile Glu Ile Ile Asp Lys Leu Ile Ser Val Pro Tyr Val Glu Met Thr<br>145                 150                 155                 160 | 480 |
| ttg aga ttg atg gag cgt ttt ggc gtg acg gca gag cat tct gat agc<br>Leu Arg Leu Met Glu Arg Phe Gly Val Thr Ala Glu His Ser Asp Ser<br>                165                 170                 175 | 528 |
| tgg gac aga ttc tac att aaa gga gga cag aag tac aag tcc cct gga<br>Trp Asp Arg Phe Tyr Ile Lys Gly Gly Gln Lys Tyr Lys Ser Pro Gly<br>            180                 185                 190 | 576 |
| aat gcc tat gtc gaa ggt gat gcc tcg agt gcg agt tat ttc ttg gct<br>Asn Ala Tyr Val Glu Gly Asp Ala Ser Ser Ala Ser Tyr Phe Leu Ala<br>        195                 200                 205 | 624 |

```
ggt gct gca atc act gga gga act gtg act gtc caa ggt tgc ggc acc    672
Gly Ala Ala Ile Thr Gly Gly Thr Val Thr Val Gln Gly Cys Gly Thr
    210             215                 220 acc agt ttg cag ggt gat gtg aaa ttt gct gag gta cta gaa atg atg    720
Thr Ser Leu Gln Gly Asp Val Lys Phe Ala Glu Val Leu Glu Met Met
225             230                 235                 240 gga gcg aag gtt aca tgg act gac act agt gta act gtt act ggt cca    768
Gly Ala Lys Val Thr Trp Thr Asp Thr Ser Val Thr Val Thr Gly Pro
                245                 250                 255 ccg cgt cag ccc ttt gga agg aaa cac ctg aaa gct gtt gat gtc aac    816
Pro Arg Gln Pro Phe Gly Arg Lys His Leu Lys Ala Val Asp Val Asn
            260                 265                 270 atg aac aaa atg cct gat gtt gcc atg act ctt gcc gtt gtt gcc ctt    864
Met Asn Lys Met Pro Asp Val Ala Met Thr Leu Ala Val Val Ala Leu
        275                 280                 285 ttt gcc gat ggt cca act gct atc aga gat gtt gcc tcc tgg aga gtg    912
Phe Ala Asp Gly Pro Thr Ala Ile Arg Asp Val Ala Ser Trp Arg Val
    290                 295                 300 aag gaa acc gag aga atg gtg gca atc tgc acg gaa cta aca aag ctg    960
Lys Glu Thr Glu Arg Met Val Ala Ile Cys Thr Glu Leu Thr Lys Leu
305             310                 315                 320 gga gca acg gta gag gaa ggc ccg gac tac tgc att atc aca cca cca   1008
Gly Ala Thr Val Glu Glu Gly Pro Asp Tyr Cys Ile Ile Thr Pro Pro
                325                 330                 335 gag aag ctg aac gtc acg gca atc gac acc tac gat gac cac cgg atg   1056
Glu Lys Leu Asn Val Thr Ala Ile Asp Thr Tyr Asp Asp His Arg Met
            340                 345                 350 gcg atg gcc ttc tcc ctc gcc gcc tgc gct gag gtg cct gtc acg atc   1104
Ala Met Ala Phe Ser Leu Ala Ala Cys Ala Glu Val Pro Val Thr Ile
        355                 360                 365 agg gac cct ggg tgc acc cgc aag acc ttc ccc aac tac ttt gac gtg   1152
Arg Asp Pro Gly Cys Thr Arg Lys Thr Phe Pro Asn Tyr Phe Asp Val
    370                 375                 380 cta agc acc tta gtg aag aac tag                                   1176
Leu Ser Thr Leu Val Lys Asn
385             390

<210> SEQ ID NO 16
<211> LENGTH: 391
<212> TYPE: PRT
<213> ORGANISM: Lolium rigidum

<400> SEQUENCE: 16

Met Leu Glu Ala Leu Asp Ala Leu Gly Leu Ser Val Glu Ala Asp Lys
1               5                   10                  15

Val Ala Lys Arg Ala Val Val Gly Cys Gly Gly Arg Phe Pro Ile
                20                  25                  30

Glu Lys Asp Ala Lys Glu Glu Val Lys Leu Phe Leu Gly Asn Ala Gly
            35                  40                  45

Thr Ala Met Arg Ser Leu Thr Ala Ala Val Val Ala Gly Gly Asn
        50                  55                  60

Ala Thr Tyr Val Leu Asp Gly Val Pro Arg Met Arg Glu Arg Pro Ile
65                  70                  75                  80

Gly Asp Leu Val Val Gly Leu Lys Gln Leu Gly Ala Asn Val Asp Cys
                85                  90                  95

Phe Leu Gly Thr Asp Cys Pro Pro Val Arg Ile Asn Gly Ile Gly Gly
            100                 105                 110

Leu Pro Gly Gly Lys Val Lys Leu Ser Gly Ser Ile Ser Ser Gln Tyr
        115                 120                 125
```

```
Leu Ser Ser Leu Leu Met Ala Ala Pro Leu Ala Leu Gly Asp Val Glu
        130                 135                 140

Ile Glu Ile Ile Asp Lys Leu Ile Ser Val Pro Tyr Val Glu Met Thr
145                 150                 155                 160

Leu Arg Leu Met Glu Arg Phe Gly Val Thr Ala Glu His Ser Asp Ser
                165                 170                 175

Trp Asp Arg Phe Tyr Ile Lys Gly Gln Lys Tyr Lys Ser Pro Gly
                180                 185                 190

Asn Ala Tyr Val Glu Gly Asp Ala Ser Ser Ala Ser Tyr Phe Leu Ala
                195                 200                 205

Gly Ala Ala Ile Thr Gly Gly Thr Val Thr Val Gln Gly Cys Gly Thr
210                 215                 220

Thr Ser Leu Gln Gly Asp Val Lys Phe Ala Glu Val Leu Glu Met Met
225                 230                 235                 240

Gly Ala Lys Val Thr Trp Thr Asp Thr Ser Val Thr Val Thr Gly Pro
                245                 250                 255

Pro Arg Gln Pro Phe Gly Arg Lys His Leu Lys Ala Val Asp Val Asn
                260                 265                 270

Met Asn Lys Met Pro Asp Val Ala Met Thr Leu Ala Val Val Ala Leu
                275                 280                 285

Phe Ala Asp Gly Pro Thr Ala Ile Arg Asp Val Ala Ser Trp Arg Val
                290                 295                 300

Lys Glu Thr Glu Arg Met Val Ala Ile Cys Thr Glu Leu Thr Lys Leu
305                 310                 315                 320

Gly Ala Thr Val Glu Glu Gly Pro Asp Tyr Cys Ile Ile Thr Pro Pro
                325                 330                 335

Glu Lys Leu Asn Val Thr Ala Ile Asp Thr Tyr Asp Asp His Arg Met
                340                 345                 350

Ala Met Ala Phe Ser Leu Ala Ala Cys Ala Glu Val Pro Val Thr Ile
                355                 360                 365

Arg Asp Pro Gly Cys Thr Arg Lys Thr Phe Pro Asn Tyr Phe Asp Val
                370                 375                 380

Leu Ser Thr Leu Val Lys Asn
385                 390

<210> SEQ ID NO 17
<211> LENGTH: 1176
<212> TYPE: DNA
<213> ORGANISM: Lolium rigidum
<220> FEATURE:
<221> NAME/KEY: CDS
<222> LOCATION: (1)..(1173)
<223> OTHER INFORMATION: Sensitive (S) biotype

<400> SEQUENCE: 17 atg ctc gag gcc ctg gac gcg ctc ggg ctc tcc gtg gaa gca gac aaa       48
Met Leu Glu Ala Leu Asp Ala Leu Gly Leu Ser Val Glu Ala Asp Lys
1               5                   10                  15 gtt gca aaa aga gct gta gtc gtc ggc tgt ggc ggc agg ttc ccg att       96
Val Ala Lys Arg Ala Val Val Val Gly Cys Gly Gly Arg Phe Pro Ile
                20                  25                  30 gag aag gat gcc aag gag gaa gta aag ctc ttc ttg ggg aac gct gga      144
Glu Lys Asp Ala Lys Glu Glu Val Lys Leu Phe Leu Gly Asn Ala Gly
            35                  40                  45 act gcg atg cgg cca ttg acg gca gct gta gta gct gct ggt gga aat      192
Thr Ala Met Arg Pro Leu Thr Ala Ala Val Val Ala Ala Gly Gly Asn
        50                  55                  60 gcg act tat gtt ctt gat gga gta cca aga atg agg gag cga cct atc      240
```

-continued

| | | |
|---|---|---|
| Ala Thr Tyr Val Leu Asp Gly Val Pro Arg Met Arg Glu Arg Pro Ile<br>65                            70                    75                   80 | | |
| ggt gac tta gtt gtc ggt ttg aaa caa cta ggt gcg aat gtt gat tgt<br>Gly Asp Leu Val Val Gly Leu Lys Gln Leu Gly Ala Asn Val Asp Cys<br>                    85                    90                   95 | 288 | |
| ttc ctc ggg acc gac tgc cca cct gtt cgt atc aac ggc att gga ggg<br>Phe Leu Gly Thr Asp Cys Pro Pro Val Arg Ile Asn Gly Ile Gly Gly<br>            100                  105                  110 | 336 | |
| cta cct ggt ggc aag gtt aag ctg tct ggt tcc atc agc agc caa tac<br>Leu Pro Gly Gly Lys Val Lys Leu Ser Gly Ser Ile Ser Ser Gln Tyr<br>         115                  120                  125 | 384 | |
| ttg agt tcc ttg ctg atg gct gct cct ttg gct ctt ggg gat gtc gag<br>Leu Ser Ser Leu Leu Met Ala Ala Pro Leu Ala Leu Gly Asp Val Glu<br>130                        135                  140 | 432 | |
| att gaa atc att gat aaa cta atc tct gtt cct tac gtt gaa atg aca<br>Ile Glu Ile Ile Asp Lys Leu Ile Ser Val Pro Tyr Val Glu Met Thr<br>145                        150                  155                  160 | 480 | |
| ttg aga ttg atg gag cgt ttt ggc gtg acg gca gag cat tct gat agc<br>Leu Arg Leu Met Glu Arg Phe Gly Val Thr Ala Glu His Ser Asp Ser<br>                    165                  170                  175 | 528 | |
| tgg gac aga ttc tac att aaa gga gga cag aag tac aag tcc cct gga<br>Trp Asp Arg Phe Tyr Ile Lys Gly Gly Gln Lys Tyr Lys Ser Pro Gly<br>                180                  185                  190 | 576 | |
| aat gcc tat gtc gaa ggt gat gcc tcg agt gcg agt tat ttc ttg gct<br>Asn Ala Tyr Val Glu Gly Asp Ala Ser Ser Ala Ser Tyr Phe Leu Ala<br>         195                  200                  205 | 624 | |
| ggt gct gca atc act gga gga act gtg act gtc caa ggt tgc ggc acc<br>Gly Ala Ala Ile Thr Gly Gly Thr Val Thr Val Gln Gly Cys Gly Thr<br>210                        215                  220 | 672 | |
| acc agt ttg cag ggt gat gtg aaa ttt gct gag gta cta gaa atg atg<br>Thr Ser Leu Gln Gly Asp Val Lys Phe Ala Glu Val Leu Glu Met Met<br>225                        230                  235                  240 | 720 | |
| gga gcg aag gtt aca tgg acc gac act agt gta act gtt act ggt cca<br>Gly Ala Lys Val Thr Trp Thr Asp Thr Ser Val Thr Val Thr Gly Pro<br>                    245                  250                  255 | 768 | |
| ccg cgt cag ccc ttt gga agg aaa cac ctg aaa gct gtt gat gtc aac<br>Pro Arg Gln Pro Phe Gly Arg Lys His Leu Lys Ala Val Asp Val Asn<br>         260                  265                  270 | 816 | |
| atg aac aaa atg cct gat gtt gcc atg act cta gcc gtt gtt gcc ctt<br>Met Asn Lys Met Pro Asp Val Ala Met Thr Leu Ala Val Val Ala Leu<br>275                        280                  285 | 864 | |
| ttt gcc gat ggt cca act gct atc aga gat gtt gcc tcc tgg aga gtg<br>Phe Ala Asp Gly Pro Thr Ala Ile Arg Asp Val Ala Ser Trp Arg Val<br>290                        295                  300 | 912 | |
| aag gaa acc gag aga atg gtg gca atc tgc acg gaa cta aca aag ctg<br>Lys Glu Thr Glu Arg Met Val Ala Ile Cys Thr Glu Leu Thr Lys Leu<br>305                        310                  315                  320 | 960 | |
| gga gca acg gta gag gaa ggc ccg gac tac tgc att atc acg cca cca<br>Gly Ala Thr Val Glu Glu Gly Pro Asp Tyr Cys Ile Ile Thr Pro Pro<br>                    325                  330                  335 | 1008 | |
| gag aag ttg aac gtc acg gcg atc gac acc tac gat gac cac cgg atg<br>Glu Lys Leu Asn Val Thr Ala Ile Asp Thr Tyr Asp Asp His Arg Met<br>         340                  345                  350 | 1056 | |
| gcg atg gcc ttc tcc ctt gct gct tgc gcc gag gtg cct gtc acg atc<br>Ala Met Ala Phe Ser Leu Ala Ala Cys Ala Glu Val Pro Val Thr Ile<br>355                        360                  365 | 1104 | |
| agg gac cct ggg tgc acc cgc aag acc ttc ccc gac tac ttt gac gtg<br>Arg Asp Pro Gly Cys Thr Arg Lys Thr Phe Pro Asp Tyr Phe Asp Val<br>370                        375                  380 | 1152 | |
| cta agc acc tta gtg aag aac tag | 1176 | |

```
Leu Ser Thr Leu Val Lys Asn
385             390

<210> SEQ ID NO 18
<211> LENGTH: 391
<212> TYPE: PRT
<213> ORGANISM: Lolium rigidum

<400> SEQUENCE: 18

Met Leu Glu Ala Leu Asp Ala Leu Gly Leu Ser Val Glu Ala Asp Lys
1               5                   10                  15

Val Ala Lys Arg Ala Val Val Gly Cys Gly Gly Arg Phe Pro Ile
            20                  25                  30

Glu Lys Asp Ala Lys Glu Val Lys Leu Phe Leu Gly Asn Ala Gly
                35                  40                  45

Thr Ala Met Arg Pro Leu Thr Ala Val Val Ala Ala Gly Gly Asn
    50                  55                      60

Ala Thr Tyr Val Leu Asp Gly Val Pro Arg Met Arg Glu Arg Pro Ile
65              70                      75                  80

Gly Asp Leu Val Val Gly Leu Lys Gln Leu Gly Ala Asn Val Asp Cys
                85                  90                      95

Phe Leu Gly Thr Asp Cys Pro Pro Val Arg Ile Asn Gly Ile Gly Gly
                100                 105                 110

Leu Pro Gly Gly Lys Val Lys Leu Ser Gly Ser Ile Ser Ser Gln Tyr
            115                 120                 125

Leu Ser Ser Leu Leu Met Ala Ala Pro Leu Ala Leu Gly Asp Val Glu
    130                 135                 140

Ile Glu Ile Ile Asp Lys Leu Ile Ser Val Pro Tyr Val Glu Met Thr
145                 150                 155                 160

Leu Arg Leu Met Glu Arg Phe Gly Val Thr Ala Glu His Ser Asp Ser
                165                 170                 175

Trp Asp Arg Phe Tyr Ile Lys Gly Gly Gln Lys Tyr Lys Ser Pro Gly
            180                 185                 190

Asn Ala Tyr Val Glu Gly Asp Ala Ser Ser Ala Ser Tyr Phe Leu Ala
        195                 200                 205

Gly Ala Ala Ile Thr Gly Gly Thr Val Thr Val Gln Gly Cys Gly Thr
    210                 215                 220

Thr Ser Leu Gln Gly Asp Val Lys Phe Ala Glu Val Leu Glu Met Met
225                 230                 235                 240

Gly Ala Lys Val Thr Trp Thr Asp Thr Ser Val Thr Val Thr Gly Pro
                245                 250                 255

Pro Arg Gln Pro Phe Gly Arg Lys His Leu Lys Ala Val Asp Val Asn
            260                 265                 270

Met Asn Lys Met Pro Asp Val Ala Met Thr Leu Ala Val Val Ala Leu
        275                 280                 285

Phe Ala Asp Gly Pro Thr Ala Ile Arg Asp Val Ala Ser Trp Arg Val
    290                 295                 300

Lys Glu Thr Glu Arg Met Val Ala Ile Cys Thr Glu Leu Thr Lys Leu
305                 310                 315                 320

Gly Ala Thr Val Glu Glu Gly Pro Asp Tyr Cys Ile Ile Thr Pro Pro
                325                 330                 335

Glu Lys Leu Asn Val Thr Ala Ile Asp Thr Tyr Asp Asp His Arg Met
            340                 345                 350

Ala Met Ala Phe Ser Leu Ala Ala Cys Ala Glu Val Pro Val Thr Ile
        355                 360                 365
```

```
Arg Asp Pro Gly Cys Thr Arg Lys Thr Phe Pro Asp Tyr Phe Asp Val
    370             375             380

Leu Ser Thr Leu Val Lys Asn
385             390
```

METHODS FOR BREEDING GLYPHOSATE RESISTANT PLANTS AND COMPOSITIONS THEREOF

CROSS-REFERENCE TO RELATED APPLICATIONS

This application claims the benefit of U.S. Provisional Application No. 60/761,216 filed on Jan. 23, 2006. This application claims the benefit of U.S. Provisional Application No. 60/761,710 filed on Jan. 23, 2006. The disclosures of the above applications are incorporated herein by reference.

INTRODUCTION

Glyphosate, N-(phosphonomethyl) glycine, is the world's most widely used herbicide. It is sold commercially under such names as RoundUp® and Touchdown®. Glyphosate is a foliar non-selective herbicide and has no activity in the soil. Glyphosate can be used pre-plant to control emerged weeds in a no-tillage planting system or post-emergence by spot and direct application to control an extensive range of weeds, as well as to control weeds in glyphosate resistant crops such as, for example, soybeans, corn, canola, and cotton. Typically, glyphosate resistant crops are designed using genetic engineering. Naturally occurring glyphosate resistant plants are very rare and such rare plants are typically weed varieties. There is a need for more glyphosate resistant crop and ornamental plants and, especially, glyphosate resistant turf and forage grasses.

SUMMARY

The present disclosure provides various embodiments of technology regarding plants having resistance to glyphosate. Various embodiments relate, for example, to grasses having economic value and other plants that comprise genetic material comprising certain amino acid sequences, comprise certain enzymes, are bred using certain non-transgenic methods, comprise aspects of certain deposited germplasm, or are produced using transgenic methods.

For example, the present disclosure provides a plant comprising a polypeptide molecule of a glyphosate resistant EPSPS enzyme, the polypeptide molecule comprising an amino acid sequence of SEQ. ID. NO. 2, or a functional portion thereof. In some embodiments, the EPSPS enzyme is not natural to the plant. SEQ. ID. NO. 2 or functional portion thereof can be encoded by a nucleic acid sequence comprising SEQ. ID. NO. 1 or a functional portion thereof. In some embodiments, the polypeptide molecule has about 80% or greater identity with SEQ. ID. NO. 2. In some embodiments, the nucleic acid sequence has about 93% or greater identity with SEQ. ID. NO. 1.

The present disclosure also provides a glyphosate resistant grass of economic value comprising a nucleic acid molecule that encodes a EPSPS enzyme. In some embodiments, the nucleic acid molecule comprises a sequence of SEQ. ID. NO. 1, or a functional portion thereof. In various embodiments, the nucleic acid molecule has greater than 97% identity with SEQ. ID. NO. 1. In some embodiments, the EPSPS enzyme can be a polypeptide molecule comprising an amino acid sequence that is essentially of SEQ. ID. NO. 2, or portion thereof.

The present disclosure also provides a glyphosate resistant plant comprising a non-transgenic glyphosate-resistant Lolium rigidum germplasm. In some embodiments, the present disclosure provides germplasm deposited in the ATCC as Penner ryegrass (PTA-8157 deposited on Jan. 19, 2007. In some embodiments the germplasm comprises a nucleic acid molecule of SEQ. ID. NO. 1, or a functional portion thereof The germplasm can comprise a polypeptide molecule of a glyphosate resistant plant EPSPS enzyme. In some embodiments, the germplasm comprises a polypeptide molecule comprising an amino acid sequence of SEQ. ID. NO. 2, or a functional portion thereof. In some embodiments, the germplasm comprises two different glyphosate resistant genes. In some embodiments, the germplasm comprises at least one glyphosate resistant protein. The germplasm can be used in a breeding program or crossed with a sexually compatible plant.

In various embodiments, the present invention provides grasses or other plants that are in a golf course fairway, a golf course rough, a golf course tee box, a lawn, an athletic field, a park, a roadside, a right of way for a utility or a railway, a trail, seed, or sod. In various embodiments, such plants are plants of economic value, including glyphosate resistant turf grass. The turfgrass can be, for example, selected from ryegrass, fescue, combinations thereof, and hybrids thereof. In some embodiments, the present disclosure provides glyphosate resistant forage grass. In some embodiments, the present disclosure provides glyphosate resistant cereal crops such as rye and wheat.

The present disclosure also provides seed of glyphosate resistant plants, as well as the mixtures comprising such seed. The present disclosure further provides progeny, vegetative sprigs, tillers, tissues cultures, cell protoplast, clones, and/or germplasm of the plants.

The present disclosure further provides methods for creating a lawn that is substantially free of a weed variety to which the lawn is susceptible. The method includes providing a lawn comprising a non-transgenic glyphosate resistant perennial turf grass and applying to the lawn a herbicidally amount of a glyphosate compound.

DRAWINGS

The skilled artisan will understand that the drawings, described herein, are for illustration purposes only. The drawings are not intended to limit the scope of the present disclosure in any way.

Figure 6:
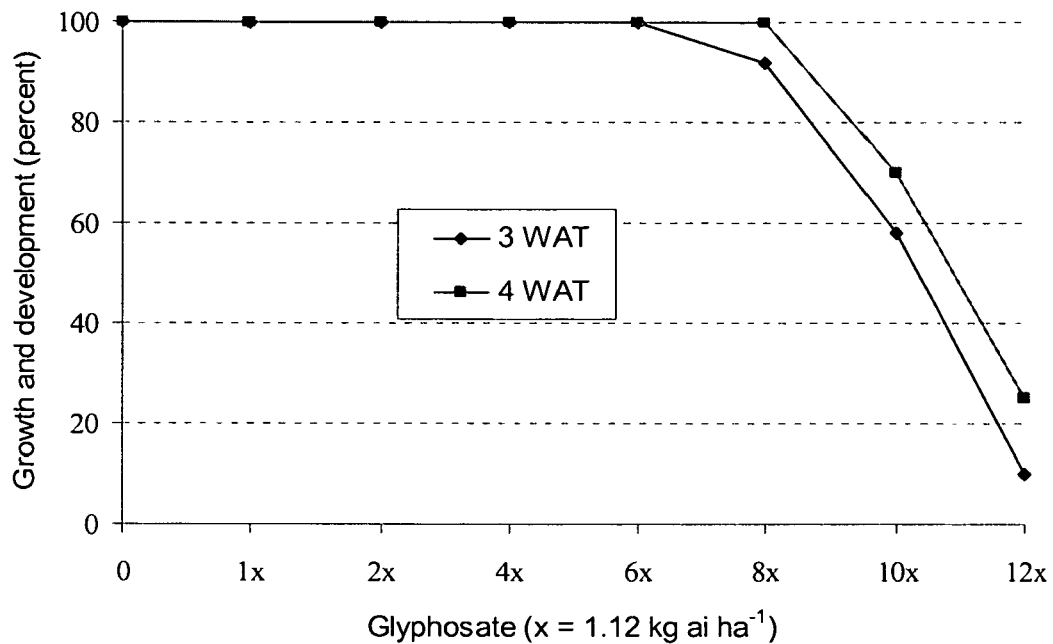
Figure 7:
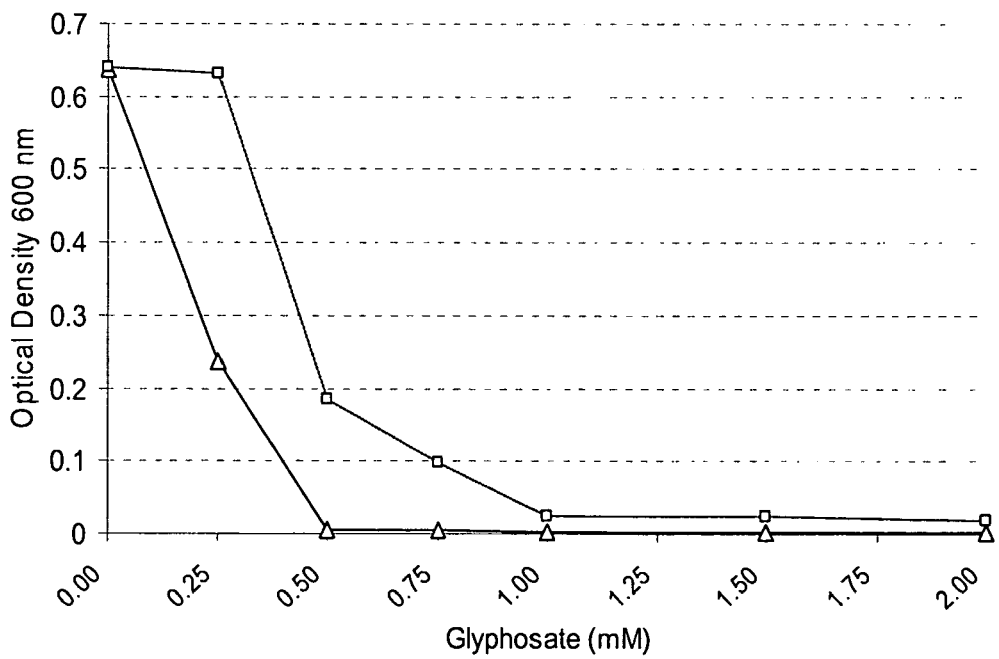

FIG. 6 is a graph illustrating a glyphosate sensitivity of the resistant (R) clone from $F_2bc_1$ hybrid 3 and 4 WAT with glyphosate; and FIG. 7 is a graph illustrating the results of expression Agrobacterium tumefaciens transformed with the glyphosate-resistant EPSPS clone (□) and wild-type *Agrobacterium tumefaciens* (◇) after growth in the presence of glyphosate for 48 hours.

Figure 8:
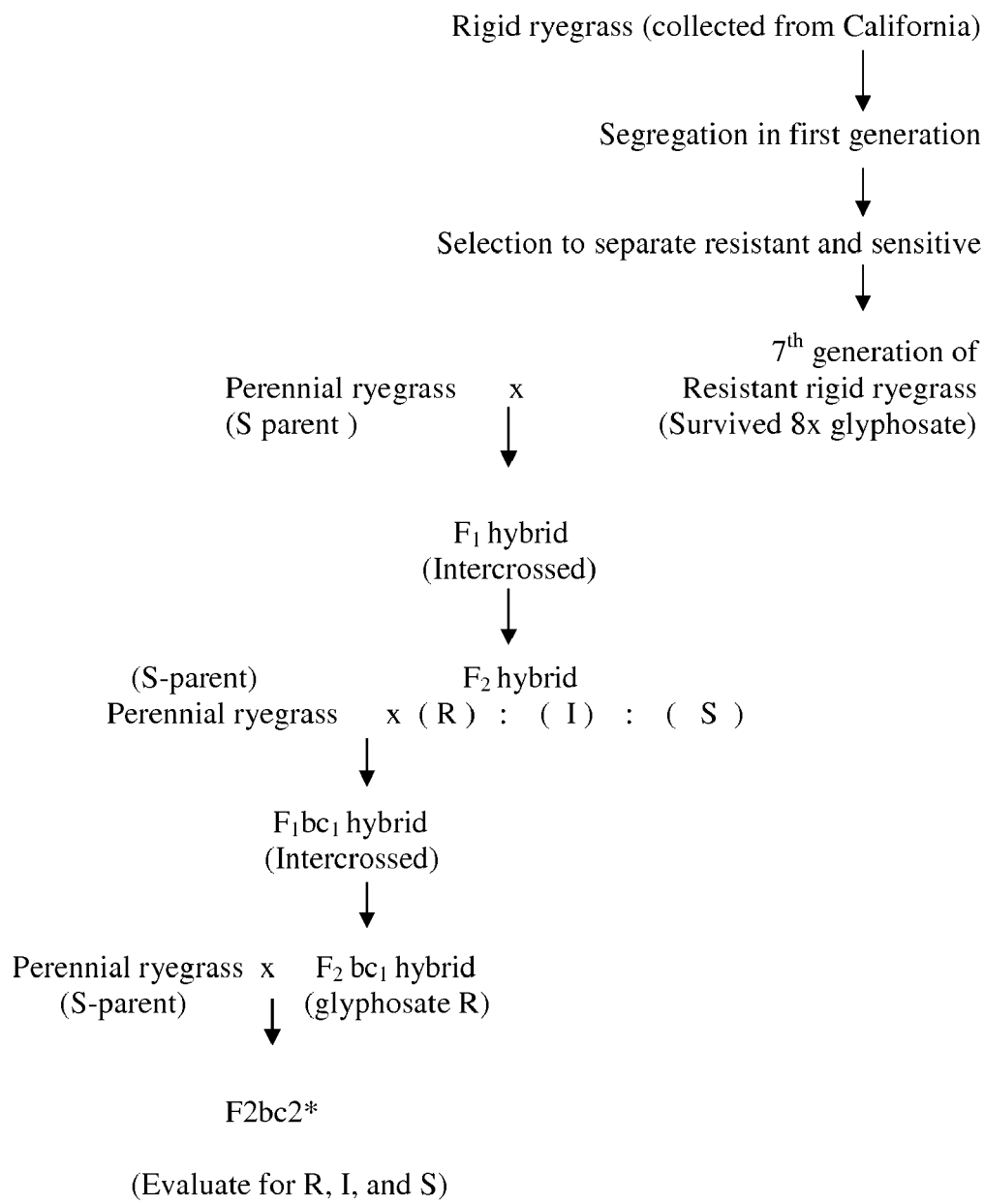

FIG. 8 illustrates a hybridization scheme between perennial ryegrass (*Lolium Perenne*) and glyphosate resistant rigid ryegrass (*L. rigidum*) from California.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein. In particular, although the present disclosure will be discussed in some embodiments as relating to glyphosate resistance in grasses, as well as plant-derived 5-enolpyruvylshikimate-3-phosphate synthase ("EPSPS") enzymes, such discussion should not be regarded as limiting the present disclosure to only such applications.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Description" section of this specification are hereby incorporated by reference in their entirety, for all purposes. In the event that one or more of the incorporated references, literature, and similar materials differs from or contradicts this application, including but not limited to defined terms, term usage, described techniques, or the like, this application controls.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

The present technology provides glyphosate-resistant plants. The term "glyphosate" as used herein refers to N-phosphonomethylglycine and its salts. Glyphosate is the active ingredient of RoundUp® herbicide (Monsanto Co.). The term "resistant" as used herein refers to a reduced toxic effect of glyphosate on the growth and development of plants.

In susceptible plant species, glyphosate inhibits biosynthesis of the aromatic amino acids tryptophan, tyrosine, and phenylalanine. In the shikimate pathway, glyphosate competes with substrate phosphoenol pyruvate, PEP, for binding site of 5-enolpyruvylshikimate-3-phosphate synthase (EPSPS; E.C. 2.5.1.19). Glyphosate is the only herbicide known to inhibit EPSPS. Metabolism of glyphosate in higher plants is very limited and not well understood. Glyphosate may not be readily metabolized if applied at phytotoxic rates. It has been reported that glyphosate metabolism to aminomethylphosonic acid ("AMPA") is slow.

After glyphosate use for more than 30 years, some species of weeds resistant to glyphosate have been reported in several countries. Glyphosate resistance has been reported for rigid ryegrass (*Lolium rigidum* Gaud.) in Australia and California, USA; for goosegrass (*Eleusine indica*) in Malaysia; for horseweed (*Conyza canadensis*) in Delaware, USA; for Italian ryegrass (*Lolium multiflorum*) in Chile; for hairy fleabane (*Conyza bonariensis*) and for buckhorn plantain (*Plantago lanceolata*) in South Africa.

The inheritance of glyphosate resistance has been studied in goosegrass from Malaysia, rigid ryegrass from Australia and horseweed in the USA. These studies concluded that the inheritance of glyphosate resistance was nuclear controlled by a single semi-dominant gene. However, it has been reported that multiple genes are responsible for glyphosate resistance in another population of rigid ryegrass from Australia.

The present disclosure provides various methods for producing plants having resistance to glyphosate. Embodiments include non-transgenic methods, transgenic methods, and methods using certain deposited material as further described herein.

The present disclosure provides glyphosate-resistant plants, including plants comprising a glyphosate resistant EPSPS enzyme that is not naturally occurring in such plants, or genetic material not naturally occurring in such plants that encodes a glyphosate resistant EPSPS enzyme. The term "plant" as used herein encompasses any higher plant and progeny thereof, including monocots such as, for example, grass, corn, rice, wheat, barley, etc.; dicots such as, for example, soybean, cotton, tomato, potato, Arabidopsis, tobacco, etc.; gymnosperms such as, for example, pines, firs, cedars, etc.; fruit such as, for example strawberries, blueberries, cherries, apples, pears, peaches, oranges and other citrus, grapes, etc.; and germplasm and other parts of such plants, including reproductive units of a plant such as, for example, seeds, bulbs, tubers, pollen, spores, corms, rhizomes, cuttings, sprigs, tillers, grafts, buds, cones, seedpods, clones, embryos, tissue cultures, endosperm, ovules, cuticles, meristems, flowers and other parts or tissues from which the plant can be reproduced. In various embodiments, the plant is an "ornamental plant" species or cultivar that is grown for its beauty in its end use, rather than having a value at harvest or as forage, in for example a garden, a park, or as a feature in a landscape design. For example, a homeowner may grow ornamental plants to beautify a home area, or a flower garden for cut flowers or for simple enjoyment. Ornamental plants include houseplants and plants used in outdoor gardening or landscaping, such as for example shrubs, flowers, evergreens, flowering trees, and grasses. In some embodiments, such plants include cereals, legumes, forage crops, oilseed crops, fiber crops, vegetable crops, grasses, turf grasses, sugarcane, sugar beet, tobacco, forest trees, fruit trees, fruit bushes, ornamental annuals, ornamental perennials and the like.

In some embodiments, the present technology provides grasses of economic value. The term "a grass of economic value" as used herein refers to a plant from the family Gramineae having an economic value (typically measured in monetary units) in a marketplace for at least one of its seed, sod, harvest, or forage. Examples of a grass of economic value include but are not limited to turfgrasses, forage grasses, wheat, rye (the cereal), rice, corn, bamboo, and ornamental grasses. In some embodiments, the present disclosure provides glyphosate resistant cereal crops such as rye, triticale and wheat. The present disclosure further provides glyphosate resistant forage grass. In some embodiments, the plant is a glyphosate resistant turf grass. A "turfgrass" is a grass when regularly mowed forms a dense growth of leaf blades and roots. Turfgrass is a major agricultural crop that covers over 50 million acres annually and is the only crop that increases with urban development. Examples of turfgrass include but are not limited to ryegrass, bent grass, zyosua, fescue, bluegrass, festolium, and bermudagrass. In various embodiments, the turf grass is a rye grass, a blue grass, a fescue, festolium, combinations thereof, hybrids thereof and derivatives thereof. A glyphosate resistant turf grass may be created by a method of this invention and then bred into other turf grass for economically desirable traits. Turfgrass can be found on, for example but not limited to, golf courses, on athletic fields, in parks, in lawns, on school grounds, roadsides, right of ways, under power lines, on trails, and maybe sold as seed or as sod. In various embodiments, the present disclosure provides grasses or other plants that are in a golf course fairway, a golf course rough, a golf course tee box, a lawn, an athletic field, a park, a roadside, a right of way for a utility or a railway, a trail, seed, or sod. In various embodiments, the present technology provides a "lawn" comprising a stand of grass having desirable, largely ornamental, features that may be planted by seed, sod or other method or maintained for commercial, residential or other purposes. In some embodiments, the lawn may be a golf course fairway, a golf course rough, a golf green, an athletic field, a park, a residential yard, or a commercial landscape.

It is understood that not all of said plants may be obtained using all methods described herein. The selection of one or more of such methods for making a given plant of the present technology is, however, within the skill of one of ordinary skill in the art. Moreover, while production of a given plant may be specifically described herein in context of a given method, it is contemplated that such plants may be made by other methods, and that other plants may be made by such methods.

Non Transgenic Glyphosate Resistant Plants and Methods of Making

The present technology provides in various embodiments, non-transgenic glyphosate-resistant plants. As referred to herein, the term "non-transgenic" refers to plants derived from other plants to obtain glyphosate resistant characteristics using breeding or similar techniques not including genetic transformation, i.e., such that the plant does not containing a transgene. Such plants are generally not considered to be a genetically modified organism ("GMO"). It is understood, however, that such plants may have characteristics that are essentially identical to transgenic plants, or may be non-transgenically derived from plants that are transgenically produced for purposes other than obtaining glyphosate resistance. In some embodiments, such plants may be hybrids.

The term "hybrid" as used herein refers to seed or plants produced as the result of inter-species fertilization as opposed to seed produced as the result of fertilization of a female gamete by a male gamete from the same species. The term "transformation" as used herein refers to a process of introducing an exogenous nucleic acid sequence (such as, for example, a vector, recombinant nucleic acid molecule) into a cell or protoplast so that exogenous nucleic acid is incorporated into a chromosome or plastid genome or is capable of autonomous replication. The terms "transformed" or "transgenic" as used herein refer to a cell, tissue, organ, or organism into which has been introduced a foreign nucleic acid, such as a recombinant vector. Transformation may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (such as, for example, particle bombardment), *Agrobacterium* infection, and the like. A "transgenic" or "transformed" cell or organism also includes progeny of the cell or organism and progeny produced from a breeding program employing such a "transgenic" plant as a parent in a cross and exhibiting an altered phenotype resulting from the presence of the foreign nucleic acid. The term "transgene" as used herein refers to any nucleic acid sequence introduced into a cell or organism via transformation. The term transgene also encompasses the component parts of a native plant gene modified by insertion of a nucleic acid sequence by directed recombination.

In various embodiments, such plants are bred or otherwise derived from grasses for the genus *Lolium*, including *Lolium rigidum*. The genus *Lolium* includes five species worldwide. They can be separated into the allogamus (self-incompatible) group including *Lolium perenne* L. (perennial ryegrass), *Lolium multiflorum* Lam. (annual ryegrass), and *Lolium rigidum* Gaud. (rigid ryegrass) and the autogamus (self-compatible) group including *Lolium tumelentum* L. and *Lolium remotum* Schrank. Allogamus plants are self-incompatible and naturally out-cross within or between species in the same genus. Ryegrass is a diploid having 14 chromosomes (2n=14), however, forage ryegrass may be a tetraploid having 28 chromosomes (4n=28). In some embodiments, the non-transgenic glyphosate resistant grass can be a rye grass hybrid and in some embodiments, a non-transgenic glyphosate resistant grass can be a hybrid wherein one parent is a glyphosate resistant *Lolium rigidum*.

The origin of rigid ryegrass has been proposed to be from Europe. Breeding methods used for the first released rigid ryegrass cultivar in the USA are natural selection and rouging. These methods identify and dispose of abnormal plants and those with desirable characteristics are used as parents to generate the following cycles. Individual plants, which have specified phenotypic characteristics, are selected from the population and used for parents of the new generation.

In some embodiments, a non-transgenic glyphosate resistant grass, e.g., turf grass, comprises a nucleic acid molecule that encodes a glyphosate resistant EPSPS enzyme. The term "encode" as used herein refers to chromosomal DNA, plasmid DNA, cDNA, or synthetic DNA from which a cell, or a complete set of transcription and translation functions in vitro, may produce any of the proteins discussed herein. Some embodiments include a plant comprising a nucleic acid molecule that encodes the glyphosate resistant EPSPS enzyme of SEQ. ID. NO. 2, and glyphosate resistant EPSPS proteins having a 80% identity thereto, and functional portions thereof. The terms "protein," "polypeptide," "peptide," "encoded product," "amino acid sequence" as used herein are used interchangeably to refer to compounds comprising amino acids joined via peptide bonds. A "protein" encoded by a gene is not limited to the amino acid sequence encoded by the gene, but includes post-translational modifications of the protein. The term "amino acid sequence" as used herein refers to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but are not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. In some embodiments the glyphosate resistant EPSPS according to the present disclosure, can include a chloroplast transit peptide (CTP). The CTP assists in carrying the EPSPS from its site of synthesis in the cytoplasm to the chloroplast. The CTP is cleaved from the EPSPS at the chloroplast to create a functional EPSPS enzyme.

In some embodiments, the nucleic acid molecule that encodes a glyphosate resistant EPSPS enzyme can include a sequence that is substantially similar to SEQ. ID. NO. 1, or a fragment thereof. In some embodiments, the nucleic acid molecule has an identity of about 93% or greater with the SEQ. ID. NO. 1 and having a serine encoded at residue position 101. In some embodiments, the nucleic acid molecule has an identity of greater than 97% with SEQ. ID. NO. 1. The term "identity" as used herein refers to the degree of similarity between two nucleic acid or protein sequences. An alignment of the two sequences is performed by a suitable computer program. The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there are 100 matched amino acids between 200 and about 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity. In some embodiments, glyphosate resistant grass of economic value comprises a glyphosate resistant EPSPS enzyme and the enzyme can be substantially similar to SEQ. ID. NO. 2, or a fragment thereof. The term "equivalent residue position" as used herein is a position that is functionally equivalent in an EPSPS enzyme to a residue position of a different EPSPS enzyme. Examples of equivalent residue position include the following: residue position 53 of SEQ. ID. NO. 2 is equivalent to residue position 101 of SEQ. ID. NO. 2. The terms "amino-acid substitutions" and "amino-acid variants" as used herein refer to preferable substitutions of single amino-acid residue for another amino-acid residue at any position within the protein. Substitutions, deletions, insertions or any combination thereof can be combined to arrive at a final construct.

In some embodiments, the non-transgenic glyphosate resistant grass comprises a functional portion of SEQ. ID. NO. 1. In some embodiments, the non-transgenic glyphosate resistant grass comprises a glyphosate resistant EPSPS enzyme that comprises a functional portion of SEQ. ID. NO. 2.

In some embodiments, the non-transgenic glyphosate resistant grass comprises a portion of a gene that encodes SEQ. ID. NO. 2 or a functional portion thereof. The term "gene" as used herein refers to a nucleic acid sequence such as, for example, chromosomal DNA, plasmid DNA, cDNA, synthetic DNA, or other DNA that encodes a peptide, polypeptide, protein, precursor or RNA molecule, and regions flanking the coding sequence involved in the regulation of expression. The term "gene" encompasses the regions of a structural gene that encode a protein and includes sequences located adjacent to the coding region on both the 5' and 3' ends for a distance of about 1 kb on either end such that the gene corresponds to the length of the full-length mRNA. A functional polypeptide can be encoded by a full-length coding sequence or by any portion of the coding sequence as long as the desired activity or functional properties of the polypeptide are retained. The term "portion" as used herein in reference to a gene refers to fragments of that gene. The fragments may range in size from a few nucleotides to the entire gene sequence minus one nucleotide.

The terms "fragment of an EPSPS gene" or "portion of an EPSPS gene" as used herein refer to a portion of a full-length EPSPS gene nucleic acid that is of at least a minimum length capable of expressing a protein with EPSPS activity. The term "enzyme" as used herein refers to molecules or molecule aggregates that are responsible for catalyzing chemical and biological reactions. A molecule that catalyzes chemical and biological reactions is referred to as "having enzyme activity" or "having catalytic activity."

In some embodiments, a non-transgenic glyphosate resistant grass comprises a polypeptide molecule of glyphosate resistant plant EPSPS enzyme. In some embodiments, the polypeptide molecule comprises an amino acid sequence substantially similar to SEQ. ID. NO. 2, or any functional portion thereof. In some embodiments, a non-transgenic glyphosate resistant grass comprises a glyphosate resistant EPSPS enzyme which has an identity to any one of SEQ. ID. NO. 2, of greater than about 80%. In some embodiments, a glyphosate resistant EPSPS enzyme may be substantially similar to at least one of SEQ. ID. NO. 2, or a functional portion thereof. In some embodiments, a non-transgenic glyphosate resistant grass comprises a polypeptide molecule comprising essentially SEQ. ID. NO. 2 that provides a glyphosate resistant enzyme. In some embodiments, the non-transgenic glyphosate resistant turf grass comprises a gene substantially similar to SEQ. ID. NO. 1 that operably encodes SEQ. ID. NO. 2. In some embodiments, the present disclosure provides an isolated nucleic acid molecule comprising SEQ. ID. NO. 1 that encodes a glyphosate resistant, plant-derived EPSPS enzyme. In some embodiments, SEQ. ID. NO. 1 is isolated from a ryegrass species. In some embodiments, SEQ. ID. NO. 1 is isolated from *Lolium rigidum*. In some embodiments, an isolated nucleic acid molecule comprising a nucleic acid sequence has an identity of greater than about 93% to SEQ. ID. NO. 1 and having a serine encoded at residue position 101. In some embodiments, an isolated nucleic acid molecule comprising a nucleic acid sequence has an identity of greater than about 97% to SEQ. ID. NO. 1.

In some embodiments, SEQ. ID. NO. 1 is isolated from germplasm of the ATCC deposit of Penner ryegrass (PTA-8157 deposited on Jan. 19, 2007). The terms plant "germplasm" or "genetic material" as used herein refer to the reproductive or vegetative propagating material of plants and includes any raw genetic material from plants required by breeders for the development of hybrids and/or improved cultivars. Plant germplasm or genetic material can be living tissue from which new plants can be grown, for example, seed or another plant part, such as, a leaf, a root, a piece of stem, pollen, ovule, a stamen, a pistil, spores, corms, rhizomes, cuttings, grafts, buds, cones, seedpods, a cuticle, a crown, a meristem, or cells that can be cultured into a whole plant, and can contain the genetic information for the plant's heredity makeup. The term "isolated" as used herein when referring to an "isolated" nucleic acid is one that has been substantially separated or purified away from other nucleic acid sequences in the cell of the organism that the nucleic acid naturally occurs such as, for example, other chromosomal and extra-chromosomal DNA and RNA, by conventional nucleic acid-purification methods. The term also embraces recombinant nucleic acids and chemically synthesized nucleic acids.

In some embodiments, the present disclosure provides an isolated polypeptide molecule comprising SEQ. ID. NO. 2 that provides a glyphosate resistant EPSPS enzyme. In some embodiments, SEQ. ID. NO. 2 is encoded by SEQ. ID. NO. 1. In some embodiments, SEQ. ID. NO. 2 is isolated from Lolium rigidum. In some embodiments, SEQ. ID. NO. 2 is isolated from germplasm of the ATCC deposit of Penner ryegrass (PTA-8157 deposited on Jan. 19, 2007). In some embodiments, an isolated DNA molecule encodes the glyphosate resistant EPSPS enzyme of SEQ. ID. NO. 2, and the isolated DNA molecule can be the nucleic acid sequence of SEQ. ID. NO. 1.

Traditional breeding methods include selecting and sowing the seeds from the strongest, most desirable plants to produce the next generation of crops. The term "selection" as used herein refers to the process of determining the relative resistance of a cultivar to glyphosate unless stated otherwise. The term "cultivar" as used herein refers to a group of plants that have certain phenotypes in common and for which those phenotypes show little to no plant-to-plant variation. The term "cultivated" as used herein refers to a plant purposely grown under agricultural conditions, as opposed to a "weed" which is unintentionally grown under agricultural conditions.

Traditional plant breeding methods include wide crosses with related wild and cultivated species for a desired trait and may involve a long process of crossing back to the commercial parent to remove undesirable genes. The term "trait" as used herein refers to an observable and/or measurable characteristic of a plant. The term "wild-type" as used herein in reference to a genotype or a phenotype common throughout a large population of individuals. A functional wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (such as, for example, altered characteristics) when compared to the wild-type gene or gene product. The term "native" as used herein refers to a naturally-occurring ("wild-type") nucleic acid or polypeptide. The term "allele" as used herein refers to a particular variant of a gene when more than one form of the gene occurs within a population. The terms "recessive," "recessive gene," and "recessive phenotype" as used herein refer to an allele that lacks a phenotype or produces a weakly expressed phenotype when two alleles for a certain locus are present at the same time as in a "heterozygote." The terms "dominant," "dominant gene," and "dominant phenotype" as used herein refer to an allele that contributes the majority of a phenotype in the presence of a second allele.

In some embodiments, breeding methods include mutation studies, composite crosses and evolutionary breeding, male sterile facilitated recurrent selection and commercial hybrids from balanced tertiary trisomics and from cytoplasmic male sterility.

In various embodiments, through breeding it is possible to combine traits found in two or more individual plants and to transmit those traits to the progeny of those plants. Hybrid breeding is an advanced form of breeding. Hybrid plants result from crosses between two different varieties or inbreeds. For example, starting from two inbred lines with poor yield their crossing results in high yielding progenies. Hybrids are often superior over non-hybrid varieties in vigor, yield, uniformity, as well as in other characters, and this is the main reason for their agricultural value. In producing hybrid seed, the two varieties are generally grown in proximity for effective pollination; one variety serves as the female (egg) parent and the other as the male (pollen) parent. Natural pollination is brought about by either wind, insects, or other animals. In the past, crossing two varieties on a large scale is a very difficult task because the plants of many crop species bear both male and female reproductive structures and are self compatible, i.e., they are capable of self-pollination as well as cross-pollination. Therefore, in order to prevent self-pollination and obtain pure hybrid seed, it may be necessary to emasculate the seed parent.

The crossing L. rigidum with L. perenne is not straightforward and does not commonly happen in nature, as the L. perenne seed requires vernalization and the flowering times of L. perenne and L. rigidum are different. Therefore, vernalization and planting of L. perenne must be controlled so as to synchronize the flowering of L. perenne and L. rigidum. The terms "F-generation" and "filial generation" as used herein refer to any of the consecutive generations of cells, tissues or organisms after a biparental cross. The generation resulting from a mating of the biparental cross (such as, for example, parents) is the first filial generation (designated as "$F_1$") in reference to a seed and its plant, while that resulting from crossing of one $F_1$ individuals to another $F_1$ individual or to the $F_1$ individual itself is the second filial generation (designated as "$F_2$") in reference to a seed and its plant. For example, an $F_2$ seed and a resulting plant are produced by self-pollination of $F_1$, while later F generations are produced from self-pollination of the immediate prior generation.

The term "tissue culture" as used herein is the maintenance or growth of tissues, in vitro, in a way that may allow differentiation and preservation of their architecture and/or function. In an example of tissue culture, meristems can be actively dividing parts (about 0.2 mm to about 1.0 cm in size), at the top of the shoot tips or root tips as well as in the axillary buds. In another example, they can be dissected under the microscope and can be regenerated on specific media to complete plants. Also in a third example of tissue culture methods, shoot tips and stem cuttings (about 0.2 mm to about 1 cm in size) can be cultivated in vitro to produce complete plantlets. The term "regeneration" as used herein refers to the process of growing a plant from a plant cell, tissue, or organ (such as, for example, plant protoplast or explant). In some embodiments of the present disclosure, methods include regenerating a non-transgenic glyphosate resistant plant or portion thereof. In some embodiments, regeneration can use tissue culture techniques that are known to those skilled in the art.

In embryo genesis, after the pollination of an egg cell with pollen a new embryo develops which contains the genetic make-up of both parents. However, in interspecific or intergeneric crosses (wide crosses) the hybrid embryo arises but dies due to the failure of forming a normal endosperm. The embryo can be rescued by early excision from the caryopsis and subsequent cultivation in vitro on an artificial media. Thereafter, a complete plantlet can be regenerated from that embryo. Alternatively, plant cells or tissues (including undifferentiated callus tissue) may be stimulated in vitro so as to develop embryos or embryogenic callus tissue. Homozygous plants may be produced via embryo culture In a double haploid system, if an egg cell is pollinated with the pollen of another species (for example wheat×maize), there will be a stimulating effect which causes the newly developing embryo to contain only the chromosomes from the female gamete (half the number of chromosomes of a normal embryo). The plant regenerated from that embryo is sterile and, through colchicine treatment, fertility of this homozygous plant is recovered. The term "endogenous" as used herein refers to materials originating from within an organism or cell. The term "exogenous" as used herein refers to materials originating from outside of an organism or cell. This typically applies to nucleic acid molecules used in producing transformed or transgenic host cells and plants.

Protoplast fusion can provide a unique tool to combine valuable traits beyond the feasibility of normal sexual crossing. Protoplast as used herein is a cell from which the cell wall has been removed. Spheroplast as used herein is a cell from which most of the cell wall has been removed. Protoplasts may be isolated from leaves or other plant tissue using cell wall degrading enzymes. Triggered by electric pulses protoplasts of two selected breeding lines can be fused in an electric field. This fusion, known as somatic hybridization, encompasses the combination of all chromosomes from both fusion partners. Therefore, the starting material should possess twice the number of chromosomes which can be achieved by specific crosses or through another culture. In another example, non-traditional crossing methods include clonal propagation of genetic self-incompatible plants as described in U.S. Pat. No. 4,499,687 (1985) for use in hybrid *Brassica* seed production.

In some embodiments, a method of breeding a glyphosate resistant perennial ryegrass comprises the following steps: providing germplasm comprising glyphosate resistant *Lolium rigidum*, crossing the germplasm with a second germplasm comprising a ryegrass to produce an $F_1$; selecting a resulting germplasm from at least one member of the $F_1$ generation that is glyphosate resistant, backcrossing a selected germplasm from the $F_i$ generation with a second germplasm comprising ryegrass to produce a $bc_i$ generation selecting a resulting germplasm from the $bc_1$ generation that is glyphosate resistant, backcrossing the selected germplasm from the $bc_1$ generation with the second germplasm comprising ryegrass to produce a $bc_2$ selecting a resulting germplasm from the $bc_2$ generation that is glyphosate resistant and providing a glyphosate resistant ryegrass. In some embodiments, backcrossing (bc) can be up to seven generations. In some embodiments, backcrossing can be mixed with forward crossing. In some embodiments, a method of breeding comprises providing a biomarker which is indicative of glyphosate resistance . In some embodiments, the germplasm comprising glyphosate resistant *Lolium rigidum* may comprise a nucleic acid which is essentially SEQ. ID. NO. 1 or a functional portion thereof.

In some embodiments, a glyphosate resistant turfgrass may be obtained by embryo culture. In some embodiments, a glyphosate resistant grass may be obtained by use of protoplast fusion. In some embodiments, the step of selecting may include spraying members of a new generation with a herbicidally effective dose of glyphosate and such a step may include a wait period such as 2, 3, 4 or more weeks to determine survival of the new generation. In some embodiments, the methods of breeding may include repeating steps of providing, crossing, selecting and backcrossing at least once. Some embodiments include the seed that is created from the breeding method. In some embodiments, the breeding method can further comprise selecting for an agronomically desirable trait. In some embodiments, an agronomically desirable trait may include drought resistance, salinity resistance, disease resistance, fungus resistance, bacteria resistance, blade height, blade width, blade color, vigor, seed production, insect resistance and winter hardiness. In some embodiments, a breeding method may include the use of a germplasm comprising a glyphosate resistant *Lolium rigidum* that comprises a molecule that is essentially part of SEQ. ID. NO. 2, or a functional portion thereof and that encodes a glyphosate resistant EPSPS enzyme.

In some embodiments, a method of breeding glyphosate resistant plants comprises the following steps: providing a material comprising a nucleic acid sequence that is essentially one of SEQ. ID. NO. 1, or a functional portion thereof and sequences having an identity of greater than 97% thereto, crossing the material with a germplasm compatible with the material and producing a glyphosate resistant germplasm. In some embodiments, the material may be selected from the following: germplasm, cuticle, seed, pollen, ovule, root, flour, tissue, meristem, endosperm, seed, cells, or another plant part. In some embodiments, the material may be selected from the following: ryegrass, fescue, festolium, combinations thereof and hybrids thereof. In some embodiments, a glyphosate resistant germplasm is a hybrid comprising of germplasm from a glyphosate resistant *Lolium rigidum* . In some embodiments, a method of producing a glyphosate resistant plant comprises the following steps: crossing a first grass plant with at least one other grass plant to produce a progeny of grass plants and such first grass plant may comprise at least one of the following SEQ. ID. NO. 2, or a functional portion thereof and sequences having an identity of 80% thereto, and screening the progeny of grass plants to select the progeny of grass plants that is resistant to glyphosate. In some embodiments, a method of breeding a plant with enhanced resistance to glyphosate comprises the following steps: providing a first plant, the first plant is a glyphosate resistant *Lolium rigidum* , crossing the first plant and the second plant to generate a hybrid plant, the hybrid plant comprising a glyphosate resistant gene and selecting a glyphosate resistant plant or derivative thereof. In some embodiments, a method of breeding can further comprise backcrossing the glyphosate resistant hybrid or a derivative thereof and a second plant to generate a backcrossed hybrid plant, the backcrossed hybrid plant comprises a naturally resistant gene, and selecting a glyphosate resistant crossed hybrid plant. In some embodiments, the second plant may be at least one of the following: ryegrass, fescue, forage ryegrass, festolium, combinations thereof, hybrids thereof and derivatives thereof.

In some embodiments, a method of breeding may further comprise exposing a first plant to colchicine or other muted gene to create a tetraploid. Exposing a diploid to tetraploid to create a tetraploid in a ryegrass is well-known in the art, see for example, Myers (1939) J. Heredity 30:499-504. In some embodiments, a method of breeding may comprise a step that includes crossing a tetraploid with a second plant that is a tetraploid to generate a hybrid plant. Such tetraploid may have value as a forge product. In some embodiments, a tetraploid may be a ryegrass, a hybrid thereof, or derivative thereof. In some embodiments, further backcrossing may be performed with a selected generation of a tetraploid and a second plant comprising a tetraploid. In some embodiments, additional crossing may be performed with a hybrid tetraploid and another plant. In some embodiments, a plant that is a tetraploid comprises a polynucleotide molecule of a glyphosate resistant plant EPSPS enzyme and a polypeptide molecule may comprise at least a sequence of at least one of SEQ.

ID. NO. 2, or a functional portion thereof. In some embodiments, a method of breeding may include a material that comprises SEQ. ID. NO. 2, or fragments thereof and sequences having an identity of 80% thereto. In some embodiments, a breeding method may include the use of a material comprising SEQ. ID. NO. 2, or fragments thereof. In some embodiments, a breeding method may include material comprising a mutation of SEQ. ID. NO. 1, or fragments thereof and sequences having an identity of 93% thereto that encode a glyphosate resistant EPSPS enzyme. In some embodiments, a breeding method may include material comprising a mutation of SEQ. ID. NO. 17, or fragments thereof that is a glyphosate resistant EPSPS enzyme. In some embodiments, a breeding method may include the use of a fescue or a fescue hybrid.

In some embodiments, a breeding method may include using a glyphosate resistant plant of the present disclosure to produce a hybrid of triticale. Techniques and methods of creating a hybrid of triticale from rye and wheat is well known to those skilled in the art and may include the use of diploids, tetraploids, hexaploids, octaploids and/or double haploids. In some embodiments, such techniques and methods may include the use of colchicine to double the chromosomes. In some techniques and methods useful herein, the wheat is used as the female parent (cytoplasm) and rye as the male parent (pollen donor) and the resulting triticale hybrid is sterile. In some cases, it may be difficult to see the expression of rye genes in the background of wheat cytoplasm and the predominant wheat nuclear genome. In some embodiments, techniques and methods useful herein may produce secalotricum in which rye cytoplasm and it is used with wheat pollen to produce triticale. In some embodiments, a resulting triticale plant or hybrid can be used to produce a non-transgenic glyphosate resistant wheat plant. Moving a trait from triticale to wheat is well known to those skilled in the art. In some embodiments, a method of breeding can produce glyphosate resistant wheat from a glyphosate resistant *Lolium rigidum* or hybrid thereof.

In some embodiments, a method for breeding resistance to glyphosate into plants comprises the following steps: selecting a plant material that constitutively expresses a glyphosate resistant enzyme, using the plant material and a breeding program, and selecting a glyphosate resistant progeny with agronomically desirable traits. In some embodiments, a method for breeding glyphosate into plants includes using plant material from ryegrass, fescue, festolium, combinations thereof, hybrids thereof and derivatives thereof. In some embodiments, a method for breeding glyphosate resistance into plants may include steps of backcrossing and further selecting. In some embodiments, the backcrossing and further selecting may be repeated multiple times until agronomically desirable traits are stable. In some embodiments, a method for breeding resistance to glyphosate into plants may include the use of plant material that is *Lolium rigidum* comprising a glyphosate resistant gene. In some embodiments, a method for breeding resistance to glyphosate into plants includes the use of a tetraploid and such tetraploid may be obtained by the use of a mutagen such as colchicine. Methods for breeding turf grass are well-known to the skilled artisan (see for example Turfgrass Biology, Genetics and Breeding ed. Cassler and Duncan (2003) and any breeding method, including those known to those skilled in the art, may be used with the glyphosate resistant material of the present disclosure.

In some embodiments, the present disclosure provides germplasm deposited in the ATCC as Penner Ryegrass (PTA-8157 deposited on Jan. 19, 2007). The germplasm is deposited in the form of seed. The germplasm can be grown into grass plants as known to those skilled in the art. In some embodiments, the germplasm is a perennial ryegrass. In some embodiments the germplasm comprises nucleic acid molecule nucleic acid molecule comprises a sequence of SEQ. ID. NO. 1, or a functional portion thereof and sequences having an identity of 93% thereto. In some embodiments the germplasm comprises a polypeptide molecule of a glyphosate resistant plant EPSPS enzyme. In some embodiments, the germplasm comprises a polypeptide molecule comprising an amino acid sequence of SEQ. ID. NO. 2, or a functional portion thereof and sequences having an identity of 80% thereto.

In some embodiments, the Penner Ryegrass can be used in a breeding program or crossed with a sexually compatible plant to produce a glyphosate resistant plant. In some embodiments, the germplasm is a perennial ryegrass. Also disclosed is a method of producing a grass plant which includes crossing a grass plant produced from the Penner Ryegrass with at least one other grass plant to produce at least one seed, harvesting the seed, and germinating the seed to produce at least one progeny grass plant. Included in the present technology are grass plants produced using this method, as well as a vegetative sprig, tiller, or clone of the grass plant. In some embodiments, the Penner Ryegrass can be used to produce a glyphosate resistant forage grass as described herein. In some embodiments, the Penner Ryegrass can be used to produce a glyphosate resistant wheat. In some embodiments, the Penner Ryegrass can be crossed with a fescue. In some embodiments, the present disclosure provides methods of producing a glyphosate resistant turf grass derived from the Penner Ryegrass. In some embodiments methods can include preparing a progeny plant derived from the Penner Ryegrass by crossing a plant of the Penner Ryegrass with a second turf grass plant, wherein a sample of the seed of the Penner Ryegrass was deposited under ATCC PTA-8157 deposited on Jan. 19, 2007; then crossing the progeny plant with itself or a second plant to produce a seed of a progeny plant of a subsequent generation and growing a progeny plant of a subsequent generation from the seed and crossing the progeny plant of a subsequent generation with itself or a second plant; and repeating steps of crossing and growing for an additional two to ten generations to produce a glyphosate resistant turf grass derived from the Penner Ryegrass.

In some embodiments, the germplasm can have more than one glyphosate resistant allele. At least one of the glyphosate resistant alleles is the single nucleotide polymorphism ("SNP") for the EPSPS gene at nt301 of SEQ. ID. NO. 1. By sequencing of the EPSPS from sensitive and resistant ryegrass biotypes the SNP was identified. A change from cytosine to thymine at this position changes the amino acid from proline to serine. The SNP at nt301 of SEQ. ID. NO. 1 can be used as a marker to identify plants that carry the allele of the resistant form of EPSPS. As shown in Table 1 and highlighted in the Examples below, a second allele can contribute to the glyphosate resistance.

TABLE 1

Comparison of the occurrence of the SNP and Glyphosate resistance for a group of backcrossed turfgrass samples.

| Sample Number | SNP Analysis (a) | Phenotype (Dead) |
|---|---|---|
| 1 S control | No | 1X |
| 2 R control | Yes | 8X |
| 3 | No | 2X |

TABLE 1-continued

Comparison of the occurrence of the SNP and Glyphosate resistance for a group of backcrossed turfgrass samples.

| Sample Number | SNP Analysis (a) | Phenotype (Dead) |
|---|---|---|
| 4 | Yes | 2X |
| 5 | Yes | 8X |
| 6 | No | 1X |
| 7 | No | 4X |
| 8 | No | 1X |
| 9 | Yes | 4X |
| 10 | No | 4X |
| 11 | Yes | 4X |
| 12 | Yes | 4X |
| 13 | No | 1X |
| 14 | No | 2X |
| 15 | Yes | 4X |
| 16 | Yes | 4X |
| 17 | Yes | 6X |
| 18 | Yes | 2X |
| 19 | No | 4X |
| 20 | No | 4X |
| 21 | No | 4X |
| 22 S control | No | 1X |
| 23 R control | Yes | 8X |

(a) See Example 5 for an example of the SNP analysis.

Having both the first allele (the SNP) and the second allele in a plant such as, for example, a turf grass, can increase resistance to glyphosate. In some embodiments, the second allele may be attributed to glyphosate oxidoreductase ("GOX") enzyme encoded by a GOX gene. Only one of the alleles may be needed to produce a glyphosate resistant plant such as for example, a turfgrass. In some embodiments, the second allele can be identified as the Gly-Rest 2 gene. The Gly-Rest 2 gene encodes a glyphosate resistant protein that can be identified as the Gly-Resist Protein ("GRP") which is different from the glyphosate resistant EPSPS. To identify which plants have only the GRP protein, the following is an example of an analysis that can be useful. The plants that have been crossed with a known glyphosate resistant parent are grown. A herbicidally effective amount of glyphosate is applied to the plants. The plants that survive the application are selected and a part of the plant is then used to determine if a biomarker for glyphosate resistant EPSPS is present. An example of such an analysis is discussed in the examples below. If the biomarker is present, then the plant has at least glyphosate resistant EPSPS and may have GRP. If the biomarker is not present, then the plant has the GRP present and does not have a detectable amount of the glyphosate resistant EPSPS present. A biomarker analysis for GRP can be designed and designing such an analysis is well within the knowledge of those skilled in the art.

In some embodiments, the present technology provides a method for creating a lawn that is substantially free of weeds. In some embodiments, a method of creating a lawn that is free of weeds includes the steps of providing a lawn comprising a glyphosate resistant turf grass and the glyphosate resistant turf grass comprises a DNA molecule that is essentially SEQ. ID. NO. 1, or a functional portion thereof, and applying to the lawn a herbicidally effective amount of a glyphosate compound.

In some embodiments, the present disclosure includes a method of obtaining a lawn that is essentially free of a weed variety to which the lawn is susceptible. In such embodiments, the lawn is essentially free of weeds. As referred to herein, a weed variety to which a lawn is susceptible is a weed that can reasonably be expected to be found in a lawn of similar grass composition, soil type, and geographic region.

The term "weed" refers to undesirable vegetative matter and may be one of the following: dandelion, goosegrass, ground ivy, clover, crabgrass, thistle, plantain, knotweed, quackgrass, nimble weed, tall fescue, creeping bent grass, zoysiagrass, bermudagrass, Dallisgrass, bindweed, black medic, carpetweed, chickenweed, creeping beggarweed, cudweed, curly dock, English daisy, evening primrose, false dandelion, filaree, Florida pusley, henbit, lambsquarters, mallow, oxalis, pennywort, pigweed, prickly lettuce, purslane, ragweed, sheep sorrel, Shepardspurse, sowthistle, speedwell, spotted spurge, tansy ragwort, wild carrot, wild geranium, wild morning-glory, wild onion, wild violet, foxtail, Johnsongrass, nutsedge, bahiagrass, barnyardgrass, poa annua, sandbur, and combinations thereof. A method of obtaining a lawn that is substantially free of weeds may include the following steps: providing a lawn comprising a glyphosate resistant turf grass, and applying to said lawn a herbicidally effective amount of a mixture comprising glyphosate. In some embodiments, a method of obtaining a lawn that is substantially free of weeds further comprises planting a seed capable of growing glyphosate resistant turf grass, wherein the turf grass is selected from ryegrass, fescue, festolium, combinations thereof, hybrids thereof and derivatives thereof. In some embodiments, a method of obtaining a lawn that is substantially free of weeds comprises providing a lawn comprising glyphosate resistant turf grass, wherein the turf grass comprises a nucleic acid molecule that encodes a glyphosate resistant EPSPS enzyme according to the present disclosure.

In some embodiments, the DNA molecules of the EPSPS glyphosate resistance gene of SEQ. ID. NO. 1 or portions thereof can be used as a probe to identify other like DNA molecules by standard methods. In some embodiments, oligonucleotide DNA molecules homologous or complementary to the EPSPS glyphosate resistance gene of *Lolium rigidum* can be used in a marker assisted breeding method to assist in the breeding of this gene into related and heterologous crop species. For example a SNP analysis can used in a marker analysis.

Transgenic Glyphosate Resistant Plants and Methods of Making

In some embodiments, the present disclosure provides a DNA construct comprising the nucleic acid molecule comprising SEQ. ID. NO. 1 that encodes a glyphosate resistant, plant-derived EPSPS enzyme and SEQ. ID. NO. 2 or a portion thereof and is operably linked to a promoter to drive expression in a host cell. In some embodiments, the present disclosure provides methods of making and using such a DNA construct. The term "construct" as used herein refers to the heterologous genetic elements operably linked to each other making up a recombinant DNA molecule. In some embodiments, the present disclosure provides methods of making and using such DNA constructs.

Through plant genetic engineering methods, it is possible to produce glyphosate resistant plants by inserting into the plant genome a DNA molecule that causes the production of higher levels of wild-type EPSPS. Examples can be found in Shah et al., *Science* 233:478-481 (1986). Glyphosate resistance can also be achieved by the expression of EPSPS variants that have lower affinity for glyphosate and therefore retain their catalytic activity in the presence of glyphosate, for example, as disclosed in U.S. Pat. Nos. 4,940,835; 5,094,945; and 5,633,435, incorporated herein by reference. Enzymes that degrade glyphosate in the plant tissues, for example, as disclosed in U.S. Pat. No. 5,463,175 are also capable of conferring cellular resistance to glyphosate. Such genes, therefore, allow for the production of transgenic crops that are resistant to glyphosate, thereby allowing glyphosate to be used for effective weed control with minimal concern of crop damage. For example, glyphosate resistance has been genetically engineered into corn as disclosed in U.S. Pat. No. 5,554,798, wheat as disclosed in Zhou et al., Plant Cell Rep. 15:159-163 (1995), soybean as disclosed in PCT Application Publication No.WO 9200377 and canola as disclosed in PCT Application Publication No. WO 9204449. Other examples of EPSPS and methods for preparing transgenic plants resistant to glyphosate include those described and/or isolated in accordance with Singh, et al., In "Biosynthesis and Molecular Regulation of Amino Acids in Plants," Amer Soc Plant Phys. Pubs (1992); U.S. Pat. Nos. 4,971,908; 5,145,783; 5,188,642; 5,310,667; 5,312,910; and 6,040,497. They can also be derived from structurally distinct classes of non-homologous EPSPS genes, such as the class II EPSPS genes isolated from *Agrobacterium sp.* strain CP4. Examples can be found in U.S. Pat. Nos. 5,633,435 and 5,627,061.

Variants of the wild-type EPSPS enzyme are glyphosate resistant as a result of alterations in the EPSPS amino acid coding sequence and examples can be found in Kishore et al., *Annu. Rev. Biochem.* 57:627-663 (1988); Schulz et al., *Arch. Microbiol.* 137:121-123 (1984); Sost et al., FEBS Lett. 173: 238-242 (1984); Kishore et al., In "Biotechnology for Crop Protection" ACS Symposium Series No. 379, eds. Hedlin et al., 37-48 (1988). These variants typically have a higher $K_i$ for glyphosate than the wild-type EPSPS enzyme that confers the glyphosate resistant phenotype, but these variants are also characterized by a high $K_m$ for PEP that makes the enzyme kinetically less efficient. For example, the apparent $K_m$ for PEP and the apparent $K_i$ for glyphosate for the native EPSPS from *E. coli* are 10 μM and 0.5μM while for a glyphosate resistant isolate having a single amino acid substitution of an alanine for the glycine at position 96 these values are 220 μM and 4.0 mM, respectively. A glyphosate resistant plant variant EPSPS gene can be constructed by mutagenesis.

Nucleotide and amino acid sequence variants of EPSPS genes and proteins, respectively, may also be used in the plants and methods of this technology. "Variant" DNA molecules are DNA molecules containing minor changes in a native EPSPS gene sequence, such as, for example, changes that one or more nucleotides of a native EPSPS gene sequence is deleted, added, and/or substituted, such that the variant EPSPS gene encodes a protein that retains EPSPS activity. Variant DNA molecules can be produced, for example, by standard DNA mutagenesis techniques or by chemically synthesizing the variant DNA molecule or a portion thereof. Methods for chemical synthesis of nucleic acids are discussed, for example, in Beaucage et al., *Tetra. Letts.* 22:1859-1862 (1981), and Matteucci et al., *J. Am. Chem. Soc.* 103: 3185-3191 (1981). Chemical synthesis of nucleic acids can be performed, for example, on automated oligonucleotide synthesizers. Such variants preferably do not change the reading frame of the protein-coding region of the nucleic acid and preferably encode a protein having no amino acid changes. Nucleic acid sequence variants are most often created for the purposes of modification of the sequence to add or delete restriction endonuclease sites or to affect transcription or translation of the nucleic acid molecule.

In some embodiments, the present disclosure provides a recombinant vector comprising the DNA construct comprising the nucleic acid molecule comprising SEQ. ID. NO. 1, or a portion thereof, that encodes a glyphosate resistant EPSPS enzyme and the recombinant vector is selected from the group consisting of plasmids, artificial chromosomes, cosmids, transposons, viruses, and combinations thereof. In some embodiments, the present disclosure provides methods of making and using such a recombinant vector.

The term "plant expression vector" as used herein refers to chimeric DNA molecules comprising the regulatory elements that are operably linked to provide the expression of a transgene product in plants. The term "chimeric" as used herein refers to a fusion nucleic acid or protein sequence. A chimeric nucleic acid coding sequence is comprised of two or more sequences joined in-frame that encode a chimeric protein. A chimeric gene refers to the multiple genetic elements derived from heterologous sources comprising a gene. The terms "in operable combination," "in operable order" and "operably linked" as used herein refer to the linkage of nucleic acid sequences in such a manner that a nucleic acid molecule capable of directing the transcription of a given gene and/or the synthesis of a desired protein molecule is produced. The terms as used herein also refer to the linkage of amino acid sequences in such a manner so that a functional protein is produced. The terms "recombinant DNA construct" or "recombinant vector" as used herein refer to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule that one or more DNA sequences have been linked in a functionally operative manner. Such recombinant DNA constructs or vectors are capable of introducing a 5' regulatory sequence or promoter region and a DNA sequence for a selected gene product into a cell in such a manner that the DNA sequence is transcribed into a functional mRNA that is translated and therefore expressed. Recombinant DNA constructs or recombinant vectors may be constructed to be capable of expressing antisense RNAs, in order to inhibit translation of a specific RNA of interest. Design of vectors useful herein include methods among those known to those skilled in the art (Plant Molecular. Biology: A Laboratory Manual, eds. Clark, Springer, New York (1997)). The term "plasmid" as used herein refers to a circular, extrachromosomal, self-replicating piece of DNA. The term "polypeptide fragments" as used herein can refer to fragments of an EPSPS that lacks at least one residue of a native full-length EPSPS protein, but that specifically maintains EPSPS activity. The terms "recombinant protein" or "recombinant polypeptide" as used herein refer to a protein molecule expressed from a recombinant DNA molecule. In contrast, the term "native protein" as used herein refers to indicate a protein isolated from a (such as, for example, a nonrecombinant) source. Molecular biological techniques may be used to produce a recombinant form of a protein with identical properties as compared to the native form of the protein. For example, SEQ. ID. NO. 2 and SEQ. ID. NO. 14 are native proteins.

In some embodiments, the present disclosure provides a recombinant vector comprising the DNA construct comprising the nucleic acid molecule comprising SEQ. ID. NO. 1, or a portion thereof, that encodes a glyphosate resistant EPSPS enzyme and the recombinant vector is selected from the group consisting of plasmids, artificial chromosomes, cosmids, transposons, viruses, and combinations thereof. In some embodiments, the present disclosure provides methods of making and using such a recombinant vector.

In some embodiments, the present disclosure provides an isolated polypeptide molecule comprising SEQ. ID. NO. 2, or a portion thereof, that provides a glyphosate resistant EPSPS enzyme. In some embodiments, SEQ. ID. NO. 2 is encoded by SEQ. ID. NO. 1, or a portion thereof. In some embodiments, SEQ. ID. NO. 2 is isolated from *Lolium rigidum*. In some embodiments, an isolated DNA molecule encodes the glyphosate resistant EPSPS enzyme of SEQ. ID. NO. 2, or a portion thereof, wherein the DNA molecule has the nucleic acid sequence of SEQ. ID. NO. 1, or a portion thereof.

In some embodiments, the present disclosure provides a recombinant DNA molecule comprising: a promoter that functions in plant cells, operably linked to a structural DNA sequence that encodes an EPSPS enzyme comprising the sequence of SEQ. ID. NO. 2, operably linked to a 3' non-translated region that functions in plant cells to cause the addition of polyadenyl nucleotides to the 3' end of the RNA sequence. In some embodiments, the present disclosure provides methods of making and using such a recombinant molecule.

In some embodiments, the present disclosure provides methods of producing a glyphosate resistant plant comprising the steps of 1) inserting into the genome of a plant cell a recombinant DNA molecule comprising: a promoter that functions in said plant cell, operably linked to a structural DNA sequence that encodes an EPSPS enzyme having the sequence of SEQ. ID. NO. 2, operably linked to a 3' non-translated region that functions in said plant cell to cause the addition of polyadenyl nucleotides to the 3' end of an RNA sequence transcribed therefrom; and 2) regenerating from the transformed plant cell a genetically transformed plant which has increased resistance to glyphosate herbicide as compared to an untransformed plant.

In some embodiments, exogenous genetic material may be transferred into a plant by the use of a plant expression vector designed for such a purpose by methods that utilize *Agrobacterium*, particle bombardment or other methods known to those skilled in the art. In some embodiments, a subgroup of exogenous material comprises a nucleic acid molecule of the present disclosure.

In some embodiments, the particular promoters selected for use in the present disclosure should be capable of causing the production of sufficient expression to, in the case of the DNA molecule, generate protein expression in vegetative or reproductive tissues of a transformed plant. A promoter is a DNA sequence that regulates RNA synthesis. Promoters or promoter regions are usually found upstream (5') to a coding sequence that controls expression of the coding sequence by controlling production of messenger RNA (mRNA) by providing the recognition site for RNA polymerase and/or other factors necessary for start of transcription at the correct site. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

Promoters may be "constitutive" or "inducible." The term "constitutive" as used herein in reference to a promoter means that the promoter is capable of directing transcription of an operably linked nucleic acid sequence in the absence of a stimulus (such as, for example, heat shock, chemicals, light, etc.). Typically, constitutive promoters are capable of directing expression of a transgene in substantially any cell and any tissue. In contrast, an "inducible" promoter is one that is capable of directing a level of transcription of an operably linked nucleic acid sequence in the presence of a stimulus (such as, for example, heat shock, chemicals, light, etc.) that is different from the level of transcription of the operably linked nucleic acid sequence in the absence of the stimulus.

In some embodiments, the DNA molecule may contain a constitutive promoter, a structural DNA sequence encoding a herbicide resistant enzyme, and a 3' non-translated region. A number of constitutive promoters that are active in plant cells have been described in the art. In some embodiments, suitable promoters for constitutive expression in plants of herbicide resistance for the DNA molecule may include, but are not limited to, the cauliflower mosaic virus (CaMV) 35S promoter (Odell et al., *Nature* 313: 810-812 (1985)).

The glyphosate target in plants, the EPSPS enzyme, is located in the chloroplast. In some embodiments, many chloroplast-localized proteins, including EPSPS, can be expressed from nuclear genes as precursors and can be targeted to the chloroplast by a chloroplast transit peptide (CTP) that is removed during the import steps, as described above. Examples of suitable such chloroplast proteins include, but are not limited to, the small subunit (SSU) of Ribulose-1,5-bisphosphate carboxylase, Ferredoxin, Ferredoxin oxidoreductase, the light-harvesting complex protein I and protein II, and Thioredoxin F. In some embodiments, it can be demonstrated in vivo and in vitro that non-chloroplast proteins may be targeted to the chloroplast by use of protein fusions with a CTP and that a CTP sequence can be sufficient to target a protein to the chloroplast. In some embodiments, incorporation of a suitable chloroplast transit peptide, such as, for example, the Arabidopsis thaliana EPSPS CTP and examples of such may be found in Klee et al., *Mol. Gen. Genet.* 210:437-442 (1987) and the Petunia hybrida EPSPS CTP and examples of such may be found in della-Cioppa et al., *Proc. Natl. Acad. Sci.* 83:6873-6877 (1986), have been show to target heterologous EPSPS protein sequences to chloroplasts in transgenic plants. In some embodiments, the production of glyphosate resistant plants by expression of a fusion protein comprising an amino-terminal CTP with a glyphosate resistant EPSPS enzyme is well known by those skilled in the art and examples of such may be found in US Pat. Nos. 5,312,910; 5,627,061; and 5,633,435, as well as EP Pat. Nos. 189707; 0218571; 508909; and 924299. Those skilled in the art will recognize that various chimeric constructs can be made that utilize the functionality of a particular CTP to import glyphosate resistant EPSPS enzymes into the plant cell chloroplast.

Nucleic acids encoding chloroplast transit peptides are readily available from genomic or cDNA of any chloroplast-targeted protein, and their sequences are well known and available, e.g., from GenBank. Further such transit peptide sequences, and their coding sequences, may be identified by algorithm-based searching, e.g., as discussed in A.I. Schein et al., "Chloroplast transit peptide prediction: a peek inside the black box," *Nucl. Acids Res.* 29(16):6 (2001), and O. Emanuelsson et al., "ChloroP, a neural network-based method for predicting chloroplast transit peptides and their cleavage sites," *Prot. Sci.* 8:978-984 (1999); alternatively, sequence analysis using the ChloroP algorithm may be performed on any sequence submitted to the ChloroP website of the Center for Biological Sequence Analysis at the Technical University of Denmark, Lyngby, DK, available online at www.cbs.dtu.dk/services/ChloroP/. Any such transit peptide, or other N-terminal peptide, may be synthesized as a fusion with an EPSPS according to some embodiments described herein.

In some embodiments, the termination of transcription is accomplished by a 3' non-translated DNA sequence operably linked in the chimeric vector to the gene of interest. In some embodiments, the 3' non-translated region of a recombinant DNA molecule contains a polyadenylation signal that functions in plants to cause the addition of adenylate nucleotides to the 3' end of the RNA. In some embodiments, the 3' non-translated region can be obtained from various genes that are expressed in plant cells. In some embodiments, the nopaline synthase 3' untranslated region and examples of such may be found in Fraley et al., *Proc. Natl. Acad. Sci.* 80:4803-4807 (1983); the 3' untranslated region from pea small subunit Rubisco gene and examples of such may be found in Coruzzi et al., *EMBO J.* 3:1671-1679 (1984); and the 3' untranslated region from soybean 7S seed storage protein gene and examples of such may be found in Schuler et al., *Nuc Acids Res.* 10:8245-8261 (1982) may be used in this capacity. In some embodiments, the 3' transcribed, non-translated regions containing the polyadenylate signal of *Agrobacterium* tumor-inducing (Ti) plasmid genes may be used in this capacity.

The aforesaid genetic elements and other regulatory elements of similar function may be substituted when appropriate by those skilled in the art of plant molecular biology to provide necessary function to the plant expression cassette. DNA constructs for glyphosate tolerance designed for expression in plasmids will necessarily contain genetic elements that function in plasmids.

In some embodiments, a vector may also include a screenable or selectable marker gene. The term "selectable marker" as used herein refers to a nucleic acid sequence whose expression confers a phenotype facilitating identification of cells containing the nucleic acid sequence. Selectable markers include those that confer resistance to toxic chemicals such as, for example, ampicillin resistance, kanamycin resistance, complement a nutritional deficiency such as, for example, uracil, histidine, leucine, or impart a visually distinguishing characteristic such as, for example, color changes or fluorescence. Useful dominant selectable marker genes include genes encoding antibiotic resistance genes such as, for example, resistance to hygromycin, kanamycin, bleomycin, G418, streptomycin or spectinomycin; and herbicide resistance genes such as, for example, phosphinothricin acetyltransferase. A useful strategy for selection of transformants for herbicide resistance is described, such as, for example, in Vasil, *Cell Culture and Somatic Cell Genetics of Plants, Vols. I-III, Laboratory Procedures and Their Applications*, Academic Press, New York (1984). Other possible selectable and/or screenable marker genes will be apparent to those of skill in the art. In some embodiments, a selectable marker may be used to monitor expression.

There are many methods for introducing transforming nucleic acid molecules into plant cells. In some embodiments of the present technology, suitable methods for transforming the nucleic acid sequence encoding EPSPS of a plant include virtually any method shown effective in introducing the nucleic acid molecules into a plant cell such as, for example, by *Agrobacterium* infection, micro projectile bombardment, or direct delivery of nucleic acid molecules.

Four general methods for direct delivery of a gene into cells have been described: (1) chemical methods and examples of such may be found in Graham et al., *Virology* 54:536-539 (1973); (2) physical methods such as microinjection and examples of such may be found in Capecchi, *Cell* 22:479-488 (1980); electroporation and examples of such may be found in Wong et al., *Biochem. Biophys. Res. Commun.* 107:584-587 (1982), Fromm et al., *Proc. Natl. Acad. Sci.* 82:5824-5828 (1985), and U.S. Pat. No. 5,384,253; and the gene gun and examples of such may be found in Johnston et al., *Methods Cell Biol.* 43:353-365 (1994); (3) viral vectors and examples of such may be found in Clapp, *Clin. Perinatol.* 20:155-168 (1993), Lu et al., *J. Exp. Med.* 178:2089-2096 (1993), and Eglitis et al., *Biotechniques* 6:608-614 (1988); and (4) receptor-mediated mechanisms and examples of such may be found in Curiel et al., *Hum. Gen. Ther.* 3:147-154 (1992); and Wagner et al., *Proc. Natl. Acad. Sci.* 89:6099-6103 (1992).

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art.

Modern *Agrobacterium* transformation vectors are capable of replication in *E. coli*, as well as *Agrobacterium*. In some embodiments, *Agrobacterium* containing both armed and disarmed Ti genes can be used for the transformations. In those plant varieties where *Agrobacterium*-mediated transformation is efficient, it is the method of choice because of the facile and defined nature of the gene transfer.

It is also to be understood that two different transgenic plants can also be mated to produce offspring that contain two independently segregating exogenous genes. In some embodiments, selfing of appropriate progeny can produce plants that are homozygous for both exogenous genes. Backcrossing to a parental plant and out-crossing with a non-transgenic plant are also contemplated, as is vegetative propagation. In some embodiments, a transgenic plant can be included in breeding methods described herein. In some embodiments, other methods of cell transformation can also be used and include, but are not limited to, introduction of DNA into plants by direct DNA transfer into pollen by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art. In some embodiments, regeneration and growth process includes the steps of selection of transformed cells, culturing those individualized cells through the usual stages of embryonic development through the rooted plantlet stage. In some embodiments, transgenic embryos and seeds can be similarly regenerated. In some embodiments, the resulting transgenic rooted shoots can be thereafter planted in an appropriate plant growth medium such as soil. The development or regeneration of plants containing the foreign, exogenous gene is well known in the art. In some embodiments, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. In some embodiments, a transgenic plant of the present disclosure containing a desired exogenous nucleic acid can be cultivated using methods well known to one skilled in the art.

Furthermore, those skilled in the art will appreciate the methods and compositions related to transformation of plants disclosed in U.S. Pat. Nos. 4,971,908; 4,769,061; 5,145,783; 5,188,642; 5,310,667; 5,312,910; 5,352,605; 5,530,196; 5,585,742; 5,792,930; 6,204,436; 6,225,114; 6,362,396; 6,426,185; 6,566,587; and 6,825,400.

Any type of cell may be used to express an improved, glyphosate-resistant EPSPS described herein from nucleic acid according to an embodiment of the present disclosure.

The cells may be separate, individual cells, or part of a multicellular assemblage, such as a callus, tissue, or organism. In some embodiments, the cells will be plant cells; in some embodiments, monocot cells. In some embodiments, the plant will be a member of the order Poales, preferably of the family Poaceae. Examples of plants from this family include bentgrass (*Agrostis* spp., e.g., *A. canina, A. palustris, A. tenuis*), Bermudagrass (*Cynodon* spp., e.g., *C. dactylon*), bluegrass (*Poa* spp., e.g., *P. pratensis, P. trivialis*), buffalograss (*Buchloe* spp., e.g., *B. dactyloides*), carpetgrass (*Axonopus* spp., e.g., *A. fissifolius*), centipede grass (*Eremochloa* spp., e.g., *E. ophiuroides*), fescue (*Festuca* spp., e.g., *F. arundinacea, F. ovina, F. rubra, F. trachyphylla*), hairgrass (*Deschampsia* spp., e.g., *D. caespitosa*), fountaingrass (*Pennisetum* spp., e.g., *P. clandestinum*, i.e. kikuyugrass), crowngrass (*Paspalum* spp., e.g., *P. notatum*, i.e. Bahiagrass; *P. vaginatum*, i.e. seashore paspalum), ryegrass (*Lolium* spp., e.g., *L. multiflorum, L. perenne, L. rigidum*), saltgrass (*Distichlis* spp., e.g., *D. spicata*), St. Augustine grass (*Stenotaphrum* spp., e.g., *S. secondatum*), and lawngrass (*Zoysia* spp., e.g., *Z. japonica, Z. matrella, Z. tenuifolia*). Nucleic acid according to some embodiments described herein can be transformed into cells, or, e.g., protoplasts thereof, by any method known useful in the art.

In some embodiments, the polypeptide, and the nucleic acid encoding it, can be isolated, naturally occurring molecules. In some embodiments, the polypeptide, and the nucleic acid encoding it, can comprise native sequences. In some embodiments, the polypeptide, and the nucleic acid encoding it, can be recombinant, and at least one of the residues specified above can be a mutation, which is not naturally occurring in the polypeptide and which is not naturally encoded by the native coding sequence of that nucleic acid.

EXAMPLES

The following examples are not limiting the present disclosure in any way. These examples may be used by one skilled in the art to better understand the present disclosure.

Example 1

Rigid ryegrass (*Lolium rigidum* Gaud.) plants are collected from an almond orchard intensively treated with glyphosate since 1984. The collected plants are grown and seed produced in greenhouse. The resistant, intermediate and susceptible biotypes are selected in the first generation using 1.12, 2.24, and 3.36 kg ai ha$^{-1}$ rates of glyphosate. Further selection is continued with a high glyphosate rate (8.96 kg ai ha$^{-1}$) to select for the resistant and with the low rate (0.28 kg ai ha$^{-1}$) to select for the susceptible individuals. The resistant (R) and susceptible (S) biotypes used in this example are generated from the 5$^{th}$ and 4$^{th}$ cycle, respectively.

R and S biotypes of the California rigid ryegrass are grown individually to the fully vegetatively mature stage prior to seedhead formation. In one experiment, two fully mature leaves of each plant (one R and one S biotypes) are treated with three 2 μl drops of glyphosate (glyphosate isopropylamine salt, ROUNDUP ULTRA™, Monsanto Co., St. Louis, Mo.) solution applied to the upper leaf surface. This corresponds to a field rate of 1.12 kg ai ha$^{-1}$ glyphosate at a volume of 187 L ha$^{-1}$ and pressure of 172.5 kPa. One week after treatment, the S biotype is dead, but no injury is observed on the R biotype.

Example 2

A dose response study is conducted on the R and S lines of rigid ryegrass. The rates of glyphosate applied varied from 0.125×, 0.25×, 0.5×, 1×, 2×, 4×, 6×, 8×, 10×, to 12×. The sprayed solutions and application procedures are similar to those described previously. Plants are evaluated for visual injury at 4 WAT. Data (4 WAT) from two experiments with 8 replications of each treatment are analyzed by non-linear regression and fitted to a log-logistic model:

$$y = \frac{100}{1 + \exp[b(\log X - \log X_{50})]}$$

where y is predictive of plant injury (% of control), $X_{50}$=dose required to obtain 50% injury and b is the slope at $X_{50}$.

The collected plants produced seeds in the greenhouse after 8 to 10 weeks. The seeds are designated as the first generation, harvested and replanted for glyphosate resistant evaluation. The percentages of survivors are 89, 59, 45, and 9 percent following glyphosate application at 1×, 2×, 4× and 8×, respectively, is shown in Table 2. Diverse sensitivity at each glyphosate level indicated that the collected plants are genetically heterozygous and that segregation occurred in the first generation.

TABLE 2

Glyphosate resistance and sensitivity of the first generation of rigid ryegrass (*Lolium rigidum*) collected from California, USA.

| Glyphosate | Survivors$^a$ | Dead plants |
|---|---|---|
| kg ai ha$^{-1}$ | percent | |
| 0 | 100 | 0 |
| 1.12 (1x) | 89 | 11$^c$ |
| 2.24 (2x) | 59 | 41 |
| 4.48 (4x) | 45 | 55 |
| 8.96 (8x) | 9$^b$ | 91 |

$^a$Data are the means of two experiments with 90 plants in each.
$^b$Plants used to generate the resistant plants (R line).
$^c$Seeds from clones used for further selection for the most sensitive plants.

Figure 1:
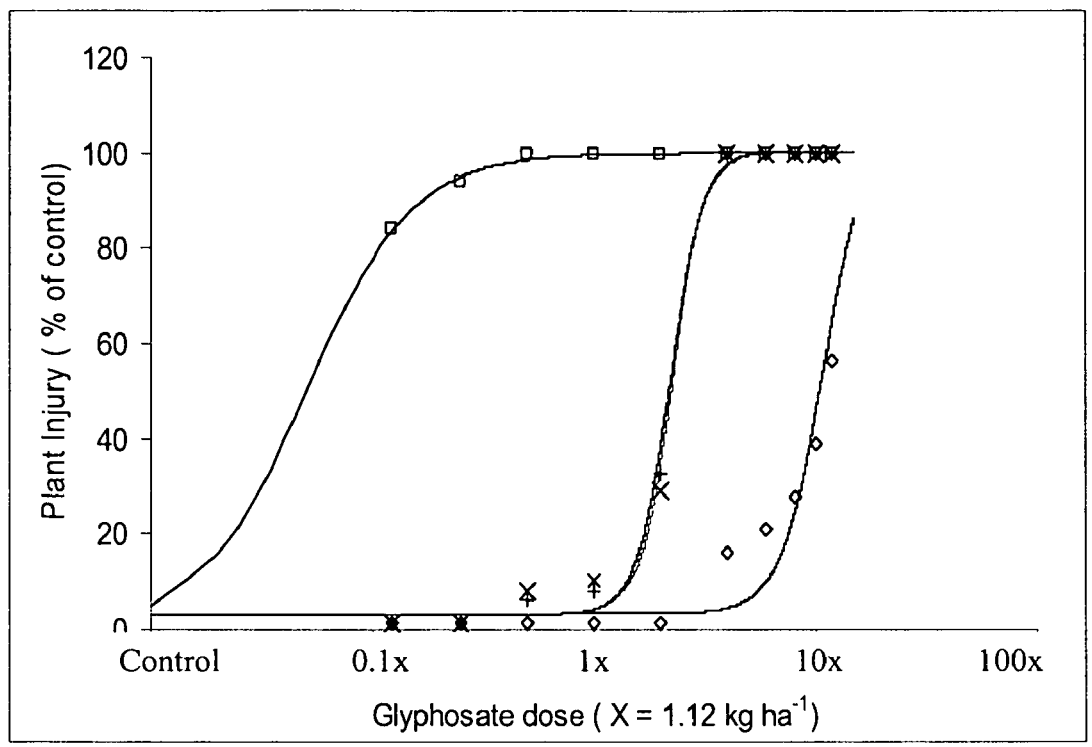
FIG. 1 is a graph illustrating a dose response curve for plant injury of resistant, sensitive, and intermediate California rigid ryegrass.

Dose response curves of the R and S lines are shown in FIG. 1. The ratio of glyphosate rates between the R and S lines for 150 (50% injury) is >100-fold (ratio of 11× to 0.1×). This >100-fold ratio indicated a very high magnitude of glyphosate resistance in rigid ryegrass generated from the California rigid ryegrass, compared to other weeds that demonstrated resistance to glyphosate as reported in, for example, Heap, *International Survey of Herbicidal Resistant Weeds* (2004) available at www.weedscience.org.

Example 3

Cross-pollination is arranged in the greenhouse between one plant each of the R and S lines which have similar maturity. To prevent pollen contamination from un-wanted ryegrass, the plants are covered with transparent plastic. The likelihood of selfing is less than 3% as discussed in, for example, Thorogood, *Perennial Ryegrass (Lolium perenne* L.) in M. D. Casler and R. R. Duncan, eds. *Turfgrass Biology, Genetics, and Breeding*, John Wiley & Sons, Inc., pp. 75-105 (2003). About 500 seeds from both R and S plants are harvested at maturity and kept separately. F$_1$ plants are grown and maintained similarly as previously described. The F$_1$ progeny are evaluated for glyphosate sensitivity when the plants are 5 to 8 cm tall. Glyphosate is sprayed at 0.125×, 0.5×, 0.25×, 1×, 2×, 4×, 6×, and 8× and the spray solutions prepared and delivered as described previously. The response of 10 plants in each of two experiments to glyphosate is recorded 3 and 4 WAT.

Twenty uniform non-sprayed plants of the $F_1$ progeny (R×S) are grown and pooled to allow intercrossing to generate $F_2$. Seeds are harvested at maturity and grown as described previously. Glyphosate sensitivity is further evaluated in the $F_2$ population. At the tillering stage, as described previously, 400 plants of the $F_2$ population are sprayed with 0.125× glyphosate (the rate used to identify the sensitive parent). The number of sensitive plants (severely injured and dead) is recorded 3 to 4 WAT. The survivors are re-acclimated for another week and re-sprayed with 8× glyphosate (the rate used to identify the resistant parent). The number of survivors is recorded 3 to 4 WAT. The remaining plants from the plant population that showed a response between sensitive and resistant rates are identified as intermediate. Expected ratios in the $F_2$ population between sensitive, intermediate, and the resistant are evaluated with the model of one or two genes involved in the inheritance of glyphosate resistance as discussed in, for example, Diggle and Neve in *Herbicide Resistance and World Grains*, S. B. Powles and D. L. Shaner, eds. CRC Press, Boca Raton, London, New York, Washington, D.C., pp. 61-99 (2001). Chi-square analyses are used to determine the most acceptable ratio for $F_2$ segregation and the inheritance of the glyphosate resistance.

The R and S lines are successfully crossed in the greenhouse. Seeds of $F_1$ progeny are harvested separately from both R and S parents. Glyphosate sensitivity in the $F_1$ progeny harvested from R parents (R×S) and from S parents (S×R) appeared to be intermediate and only survived up to 2× glyphosate. Plants of the $F_1$ progeny from (R×S) and (S×R) ranged in injury from 0 to 10% and 50 to 60% from 1× and 2× glyphosate, respectively, 3 WAT. The injury from 2× glyphosate decreased to 20-30%, 4 WAT, and full recovery is observed after 5 weeks. Glyphosate at 4× and higher rates killed the $F_1$ plants. The data indicated that the inheritance of glyphosate resistance in California rigid ryegrass is partial dominance and pollen transmitted, with no indication of maternal inheritance.

Non-sprayed $F_1$ progeny (20 plants) from R×S are intercrossed to produce $F_2$. Glyphosate sensitivity evaluation and Chi-square analysis of the $F_2$ population are shown in Table 3. Plants that died from 0.125× and those that survived 8× of glyphosate are designated genotypically similar to the R and S parents, respectively. The rest of the plants in the population are identified as intermediate between sensitive and resistant plants. The expected ratio and Chi-square analysis based on Mendelian segregation are shown in Table 3.

intermediate (between R and S), and 21 plants are resistant (survived 8× glyphosate). These numbers are tested against the hypothesized distribution ratio of (1/4): (2/4): (1/4) and (1/16): (14/16): (1/16) associated with inheritance by one or two genes, respectively. Values of the $\chi^2$ ($\chi^2=0.8$; $0.75<P<0.90$) with the tested ratio (1/16): (14/16): (1/16) indicated that at least two genes are involved in the inheritance of glyphosate resistance as shown in Table 3. The involvement of multiple genes for glyphosate resistance in the California rigid ryegrass is similar to the results reported by, for example, Feng et al., *Weed Sci.* 47:412-415 (1999) and Pratley et al., *Weed Sci.* 47:405-411 (1999) for rigid ryegrass from Australia, but is different from the inheritance study published by Lorraine-Colwill et al., *Theor. Appl. Genetics* 102:545-550 (2001), who concluded that the inheritance of glyphosate resistance in rigid ryegrass involved a single semi-dominant gene.

Example 4

Total RNA is isolated from the crown tissue of California rigid ryegrass vegetative maturity as described previously. The methods for RNA isolation are modified from methods discussed in Chomczynski and Sacchi, *Anal. Biochem* 162-156-159 (1987). Poly A mRNA is isolated from total RNA by using Oligotex mRNA Mini Kit (QIAGEN Inc, Valencia, Calif.), the procedures followed manufacturer recommendations. The quantity and quality of mRNA is determined spectrometrically.

The first strands of cDNA are synthesized from poly A mRNA using the 5'/3' RACE PCR kit (Roche Applied Science, Penzberg, Germany). Procedures for synthesis of the first strands cDNA followed the kit recommendation. It started with transcription of the mRNA using dT-anchor and reverse transcriptase in the reaction buffer provided. The first strand of cDNA is used as a template for the PCR to amplify the main fragment of EPSPS coding region using forward and reverse oligonucleotides (FP1 and reverse RP1 primers, respectively (Integrated DNA Technologies, Inc., Iowa)). The PCR mixtures including cDNA template, primers, buffer (Promega Corp., Madison, Wis.), dNTP (nucleotides mix (Promega Corp., Madison, Wis.)), and Taq polymerase (Promega Corp., Madison, Wis.) are developed in the thermocycle with temperatures adjusted as the manufacturer recommended for the primers. If annealing temperature of the primers are more than 1.0 C apart, the reactions are assigned by touch-down PCR as discussed in, for example, Don et al., *Nucl. Acid Res.* 19(14):408 (1991). PCR products are sub-

TABLE 3

Chi-square analysis of the F2 population generated from hybridization between the resistant (survived 8x glyphosate) and the sensitive (dead from 0.125x glyphosate) biotypes of rigid ryegrass (*Lolium rigidum* Gaud.) from California.

|  | Sensitive (0.125x) | Intermediate (0.125x-8x) | Resistant (8x) | Total | P value |
|---|---|---|---|---|---|
| $F_2$ (Observed) | 27 | 352 | 21 | 400 |  |
| $F_2$ (Expected)[a] | 100 (1/4) | 200 (1/2) | 100 (1/4) | 400 |  |
| $\chi^2$ | 53 | 116 | 62 | 231 na |  |
| $F_2$ (Expected)[b] | 25 (1/16) | 350 (14/16) | 25 (1/16) | 400 |  |
| $\chi^2$ | 0.2 | 0.01 | 0.6 | 0.8 aa | 0.75 < P < 0.9 |

[a]Model used for the expected ratio of segregation in the $F_2$ population if one gene is involved in the inheritance of glyphosate resistance: Resistant (RR): Intermediate (Rr): Sensitive (rr) = 1/4: 2/4: 1/4, na: hypothesis not accepted, aa: hypothesis accepted.
[b]Model used for the expected ratio of segregation in the $F_2$ population if two genes are involved in the inheritance of glyphosate resistance: Resistant (RRRR): Intermediate (RRRr + RRrr + Rrrr): Sensitive (rrrr) = 1/16: 14/16: 1/16
na: hypothesis not accepted; aa: hypothesis accepted.

In the $F_2$ population of 400 plants intercrossed from R×S, 27 plants are sensitive (died from 0.125× glyphosate), 352 are jected to electrophoresis to identify a successful amplification by visualization of a clear band under UV light. The band is excised and DNA is gel extracted using the kit (from 5'/3' RACE PCR kit). The extracted DNA from PCR products are sequenced at the Genomic Technology and Support Facilities, ("GTSF"), Michigan State University.

Figure 2:
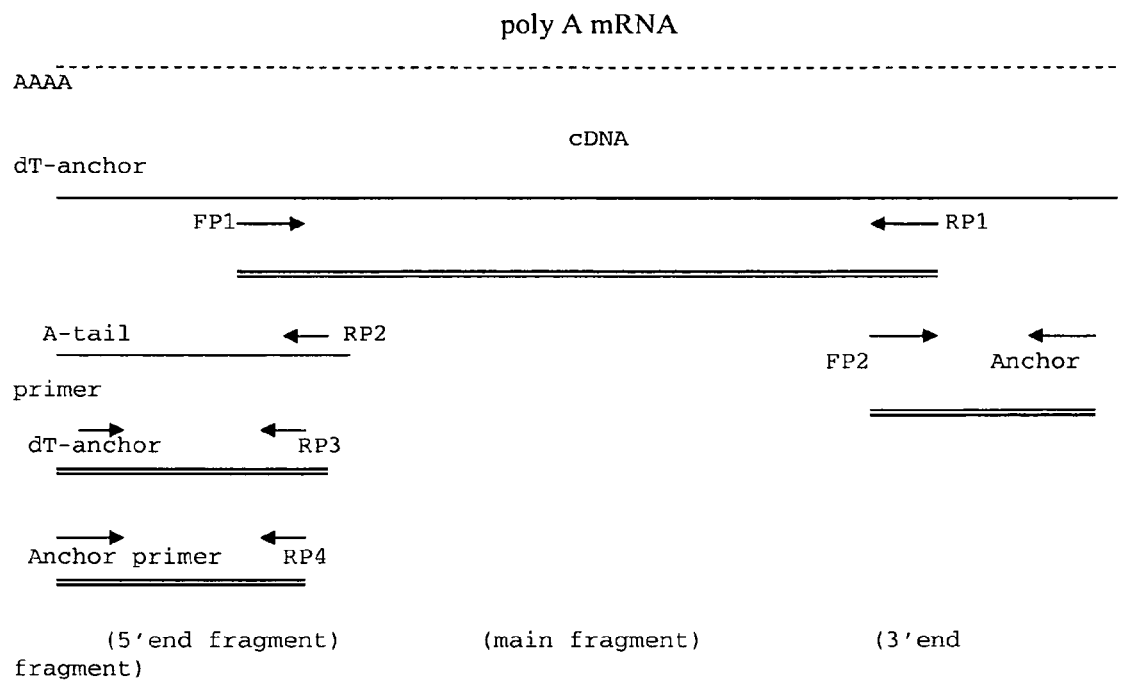
FIG. 2 illustrates a scheme of 5'/3' Random Amplification cDNA End Polymerase Chain Reaction (RACE PCR) of an EPSPS gene from rigid ryegrass.

The 3' end of EPSPS gene is generated by 3' RACE PCR using the first strand cDNA as a template as illustrated in FIG. 2. Forward oligonucleotide primers (FP1 (SEQ. ID. NO. 3); FP2 (SEQ. ID. NO. 4); FP3 (SEQ. ID. NO. 5)) are constructed from the main fragment of EPSPS coding region sequenced previously, and an anchor primer (SEQ. ID. NO. 10) is provided in the kit and is used as a reverse primer. The PCR mixtures are developed in thermo-cycle as mentioned previously, which temperatures adjusted as the manufacturer recommended. Amplification products are electrophorized and further processed, as described previously.

The 5' end of EPSPS coding region is generated by 5' RACE PCR. Reverse oligonucleotide primers (RP2 (SEQ. ID. NO. 6), RP3 (SEQ. ID. NO. 7), and RP4 (SEQ. ID. NO. 8)) are constructed from the main fragment of the EPSPS coding region, which are sequenced previously. The strand of 5' end cDNA is synthesized from mRNA using primer RP2 and reverse transcriptase in the buffer reaction as mentioned previously. Poly A-tails are attached at the 5' end of cDNA strands in the reaction of dATP nucleotides and terminal transferase, which are provided in the same kit as mentioned previously. PCR are generated to amplify 5' end EPSPS coding region using the strand of 5' end cDNA as a template, dT-anchor (SEQ. ID. NO. 9) and RP3 as forward and reverse primers, respectively. For better amplification of 5' end EPSPS gene, nested PCR is generated with the current PCR product as a template, anchor primer and RP4 as forward and reverse primers, respectively. Temperatures for amplification of PCR mixtures are adjusted as the manufacturer recommended. Amplification products from nested PCR are electrophorized, visualized and further processed as described previously.

To confirm the sequences from the PCR products, the main fragments, 5' end, and 3' end of EPSPS coding regions are cloned into a plasmid by using the pGEM Easy Vector System II (Promega Corp., Madison, Wis.). The fragments from PCR products are ligated in to the vectors, and then transformed into JM109 Competent Cells and grown on bacto-agar plates which contain antibiotics, IPTG, and X-gal. After 24 h cultured at 37° C., the growth of white colonies indicated successful transformations, while the blue colonies indicated failure. The white colonies are further grown in the LB media containing antibiotics with shaking at 37° C. for 24 h. The plasmid DNA is then extracted using the extraction kit (QIAGEN Inc., Valencia, Calif.). The insert fragments are sequenced at the GTSF, Michigan State University.

Example 5

A SNP assay was used to determine a single nucleic polymorphism ("SNP") for the EPSPS gene at nt301 of SEQ. ID. NO. 1 in a target/test plant. By sequencing of the EPSPS from sensitive and resistant ryegrass biotypes the SNP was identified. A change from cytosine to thymine at this position changes the amino acid from proline to serine. The SNP at nt301 of SEQ. ID. NO. 1 can be used as a marker to identify plants that carry the resistant form of EPSPS.

Leaf tissue is harvested from target/test plants growing in the greenhouse. DNA is extracted either by using the QIAGEN DNeasy® plant mini kit or Whatman® FTA® Elute Micro Cards. Standard protocol is used for purification of total DNA from plant tissue using the manufacturers recommendations (QIAGEN Sciences, Maryland, USA or Whatman Inc., Florham Park, NJ, USA).

Starting with a minimum of 10 mg of plant tissue, 5 parts of PBS buffer is added to 1 part of plant tissue. Leaf material is ground to a homogenate using a micropestle and microfuge tube. The homogenate is applied to the FTA® Elute Micro Card matrix inside the marked circle. Any remaining semi-homogenized tissue is pressed against the card and then discarded. The FTA cards are air dried for two hours at room temperature. DNA is eluted from the FTA cards according to the recommended protocol except that instead of a single, 3 mm diameter punch, two punches of 2 mm diameter are processed per sample (2 mm punch tool from Roboz Surgical Instrument Co. Inc. Gaithersburg, Md., USA, catalog # 65-9902). Two punches from unused Whatman FTA paper are used after each sample to minimize cross-contamination. Processing of the punches in 1.5 ml microcentrifuge tubes, the DNA is eluted using sterile water. The concentration of DNA is estimated using a spectrophotometer.

SNP Assay

A Custom TaqMan® SNP genotyping assay is developed based on the manufacturers recommendations (Applied Biosystems, Foster City, CA, USA). Five microliters DNA of each sample is transferred to wells of a 384-well plate (Applied Biosytems 384-well Optical reaction plates, catalog # 4309849), in duplicate, and are allowed to air-dry at room temperature. SNP genotyping assays are performed by adding 5μl of reaction master mix to each well of the 384-well plate [2.5 μl of Taqman Universal Master Mix with no AmpErase® UNG (2×), 0.125 μl of 40X Assay Mix (primers and Taqman probe, 40X), and 2.375 μl Molecular biology grade water]. Primers and Taqman probes are designed and synthesized by Applied Biosystems "Assay-by-Design" service (Forward primer: CGGCAGGTTCCCGATTGA (SEQ. ID. NO. 11); Reverse primer: GCATTTCCACCAGCAGCTACTA (SEQ. ID. NO. 12); VIC®-labeled Taqman probe: CCGTCAATGGCCGCAT (SEQ. ID. NO. 13); and FAM®-labeled Taqman probe: CCGTCAATGACCGCAT (SEQ. ID. NO. 14)). The plate is sealed (Applied Biosystems MicroAmp optical adhesive film, catalog # 4311971), is vortexed briefly, and is centrifuged briefly.

Real-time PCR is performed in an Applied Biosystems 7900HT Sequence Detection System, using the passive reference dye, ROX, and 9600 emulation off (Cycling parameters: 50° C. for 2 minutes, 95° C. for 10 minutes; 40 cycles of: 92° C. for 15 seconds and 60° C. for 1 minute). Allelic discrimination analysis is performed using the Applied Biosystems SDS software (v2.1).

Example 6

Extraction methods for EPSPS are modified from methods discussed in Boerboom et al., *Weed Sci.* 38:463-467 (1990). Crown tissue (0.5 gram fresh weight per sample) is harvested from California rigid ryegrass plants, frozen in liquid nitrogen, and grounded in a cold mortar with 150 mg polyvinylpolypyrrolidone (PVPP). The fine powder tissue is ground further in 0.5 ml extraction buffer (pH 7.5) containing 10 mM Trizma HCl, 1 mM ethylenediaminetetraacetic acid (EDTA), 10% (v/v) glycerol, 1 mg ml$^{-1}$ bovine serum albumin (BSA), 10 mM ascorbate, 1 mM benzamidine (BAM), and 5 mM dithiothreitol (DTT). The mixture is centrifuged at 15,000×g for 10 min, and the supernatant is desalted in 1.0 ml Sephadex G-50 column ($^7$ MICRO-SPINS® Shephadex G-50 column, Life Science Products Inc., Frederick, Colo.) and further centrifuged at 1,000×g for 3 min. Total protein in the supernatant is quantified spectrometrically at 595 nm followed the method discussed in Bradford, *Anal. Biochem* 72:248-254 (1976).

Assay of EPSPS activity is modified from methods discussed in Westwood and Weller, *Weed Sci.* 45:2-11 (1997). Reaction of shikimate 3-phosphate (S3P) and phosphoenol pyruvate (PEP) is assayed in micro-tubes using 10 µl enzyme extract in a pH 7.5 buffer. The reaction mixtures contained 50 mM HEPES, 1 mM $(NH_4)_6Mo_7O_{24}$, 5 mM KF, 1 mM PEP, 1 mM S3P and glyphosate at 0, 5, 50, 500, and 5000 µM. Reaction mixtures are incubated at 25° C. for 20 min, stopped in water bath at 100° C. for 2 min, and centrifuged at 15,000×g for 10 min for sedimenting denatured protein. The reaction of S3P and PEP is quantified by determining the remaining PEP in the mixtures, which is analyzed spectrophotometrically at 340 nm by adding NADH, pyruvate kinase and lactate dehydrogenase (PK/LDH). Reaction control used denatured plant extract (after preheated in thermo-cycle at 100° C. for 3 min) in the reactions. Enzymatic activity of EPSPS is expressed in enzyme unit (EU) per mg protein, 1 EU is equal to 1 mole of PEP used per min in the assayed reaction.

Data from duplicate experiments with three replications of each treatment are analyzed by non-linear regression and fitted to a log-logistic model, $$y = \frac{100}{1 + \exp[b(\log X - \log X_{50})]}$$

where y is predictive of EPSPS activity (% of control), $X_{50}$=concentration of glyphosate required to obtain 50% inhibition of EPSPS activity, and b is the slope at $X_{50}$.

Figure 3:
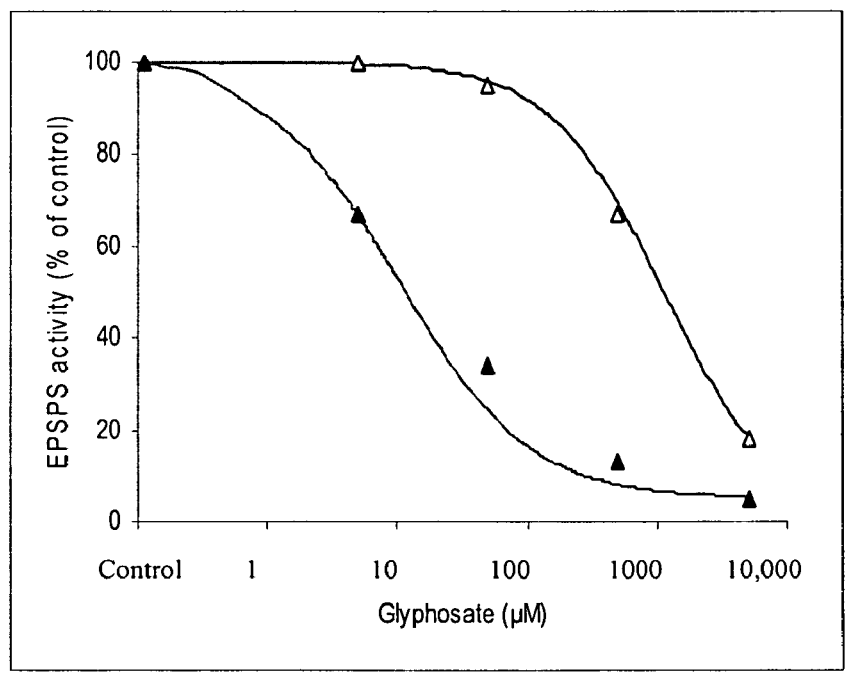
FIG. 3 is a graph illustrating EPSPS activity of glyphosate resistant (R) and sensitive (S) biotypes of the California rigid ryegrass in the presence of glyphosate.

Evaluation of the activity of the constitutive EPSPS from R and S biotypes of rigid ryegrass showed that the EPSPS is significantly inhibited more in S than in R in the presence of glyphosate from 5 to 5000 µM as shown in FIG. 3. Decreased sensitivity levels of EPSPS in R plants appeared to be a major contributor to glyphosate resistance in California rigid ryegrass. This is in contrast to the results reported with Australian rigid ryegrass as discussed in, for example, Baerson et al., *Weed Sci.* 50:721-730 (2002) and Lorraine-Colwill et al., *Pestic. Sci.* 55:486-503 (1999), and has dramatically and unexpectedly more glyphosate resistance (about 2 orders of magnitude) than the reports about glyphosate resistant goosegrass from Malaysia as discussed in, for example, Baerson et al. *Plant Physiol.* 129:1265-1275 (2002).

Example 7

The R biotype of California rigid ryegrass, which survived 8× glyphosate and perennial ryegrass, which died from 0.25× of glyphosate, are grown individually in 950-ml pots with professional planting mix media as discussed above. Plants are maintained in greenhouse with supplemental light, watered daily, and fertilized weekly with NPK water soluble fertilizer (20-20-20). At the mature vegetative stage, perennial ryegrass plants are vernalized in the growth chamber with the temperature 4 ±1 C, 8 h day and 16 h night. After 4 weeks vernalization, the plants are removed and maintained in greenhouse until flowering. Glyphosate rigid ryegrass plants do not need vernalization for onset of flowering.

Seed heads of perennial ryegrass are designated to be pollinated by California rigid ryegrass also vice-verse because both of the species are allogamus plants. Both are known to be self-incompatible. After the emergence of seed heads and before the pollen opened, one plant from each species is isolated in one room of greenhouse. To provide conditions for cross-pollination, perennial ryegrass and rigid ryegrass plants are placed next to each other. During the pollination period, plants are maintained regularly as mentioned previously until the seed reached the maturity. The successful hybridization is indicated with the full development of mature seeds which had brown color. Seeds are harvested from both perennial and rigid ryegrass. Seeds from perennial ryegrass hybrids are used for further evaluation.

Seeds of the $F_1$ hybrid harvested from perennial ryegrass are grown and maintained as individual plants in the greenhouse as described previously. At the tillering stage, 50 plants for each of glyphosate rates (0.25, 0.5, 1.0, 1.5, 2.0, 4.0, and 8×, where x=1.12 kg $ha^{-1}$) are evaluated for sensitivity or resistance. Glyphosate is delivered in 187 L $ha^{-1}$ spray solutions with 172.5 kPa pressure using a flat fan nozzle. The dead or survivors in each treatment are counted 3 weeks after treatment and the plants with the highest level of resistance are further maintained and intercrossed to generate $F_2$.

The population of $F_2$ is evaluated for glyphosate sensitivity with 0.5× glyphosate. Severely injured and dead plants are recorded 3 weeks after treatment (WAT) and are designated similar to the sensitive (S) parent. The survivors are re-acclimated for further evaluation at 8× glyphosate. The survivors from 8× glyphosate are designated similar to resistant (R) parent. The rest of the population that responded between S and R are identified as intermediate (I).

The inheritance of glyphosate resistance trait is evaluated based on Mendelian segregation ratio in the $F_2$ population. Expected ratios between sensitive, intermediate, and the resistance are hypothesized with one, two, or more than two genes involved. Chi-square analyses are used to determine the most acceptable ratio for $F_2$ segregation.

The resistant plant from $F_2$ population is backcrossed to the S parent (perennial ryegrass). Procedures for vernalization and pollination are similar to what is described above. Plants of the $F_1$ hybrid from the backcross ($F_1bc_1$) are allowed to intercross to generate $F_2$ ($F_2bc_1$). The inheritance of glyphosate resistance traits is evaluated in the $F_2bc_1$ population. Glyphosate sensitivity is evaluated at 0.25× and 8× glyphosate. Data collection and genetic evaluation are similar to the procedures as described above.

Hybridization between perennial ryegrass and glyphosate resistant rigid ryegrass from California is successfully performed in greenhouse (see FIG. 8).

The glyphosate resistant traits are transferred via cross-pollination to perennial ryegrass. Plants of the $F_1$ hybrid harvested from perennial ryegrass showed intermediate resistant level and 90 percent survived to glyphosate 2× (see Table 5).

TABLE 5

Glyphosate sensitivity or resistance in the $F_1$ population (hybridization of perennial ryegrass and glyphosate resistance rigid ryegrass)

| Glyphosate | Severely injured and dead | Survivors |
|---|---|---|
| kg $ha^{-1}$ | Percent*) | |
| 0 | 0 | 100 |
| 0.25 | 0 | 100 |
| 0.50 | 6 | 94 |
| 1 | 10 | 90 |
| 2 | 10 | 90**) |
| 4 | 100 | 0 |
| 8 | 100 | 0 |

Figure 4:
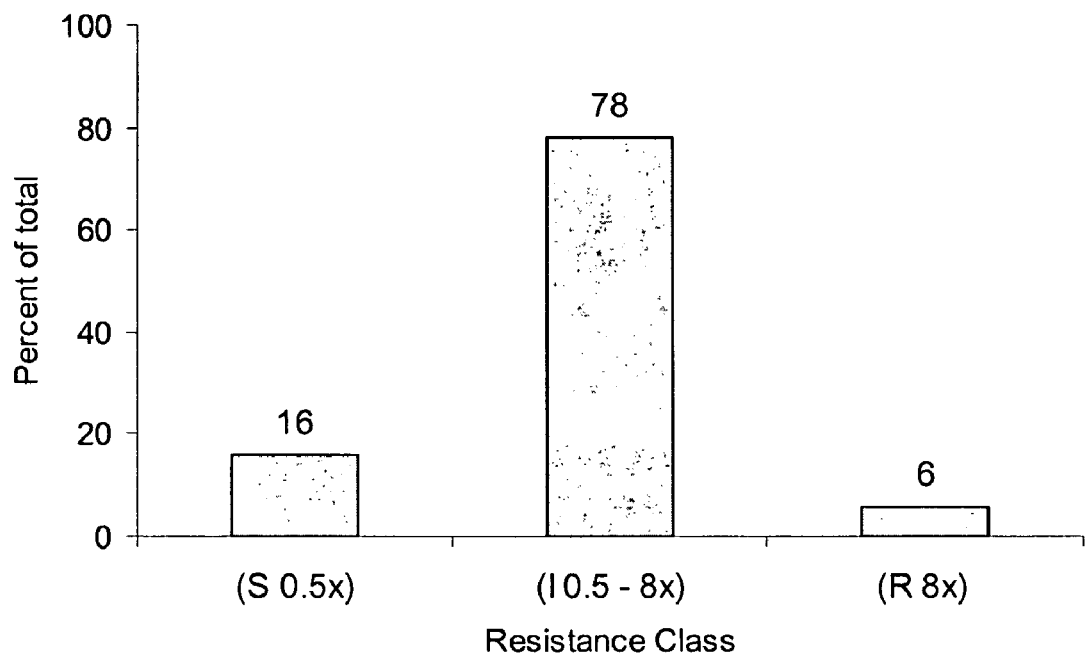
FIG. 4 is a graph illustrating the distribution of glyphosate resistant classes in a $F_2$ population of plants from a cross between perennial ryegrass and glyphosate resistant rigid ryegrass.

*) percent of the total (50 plants per treatment)
**) intercrossed to generate $F_2$ hybrid Segregation of glyphosate sensitivity in the F₂ population is illustrated in FIG. 4. The percentage of the sensitive plants in $F_2$ (16 percent) is higher than expected due to the glyphosate rate (0.5×) exceeded the sensitivity level of sensitive parents. Further evaluation showed that sensitivity level of perennial ryegrass is 0.25× glyphosate.

Figure 5:
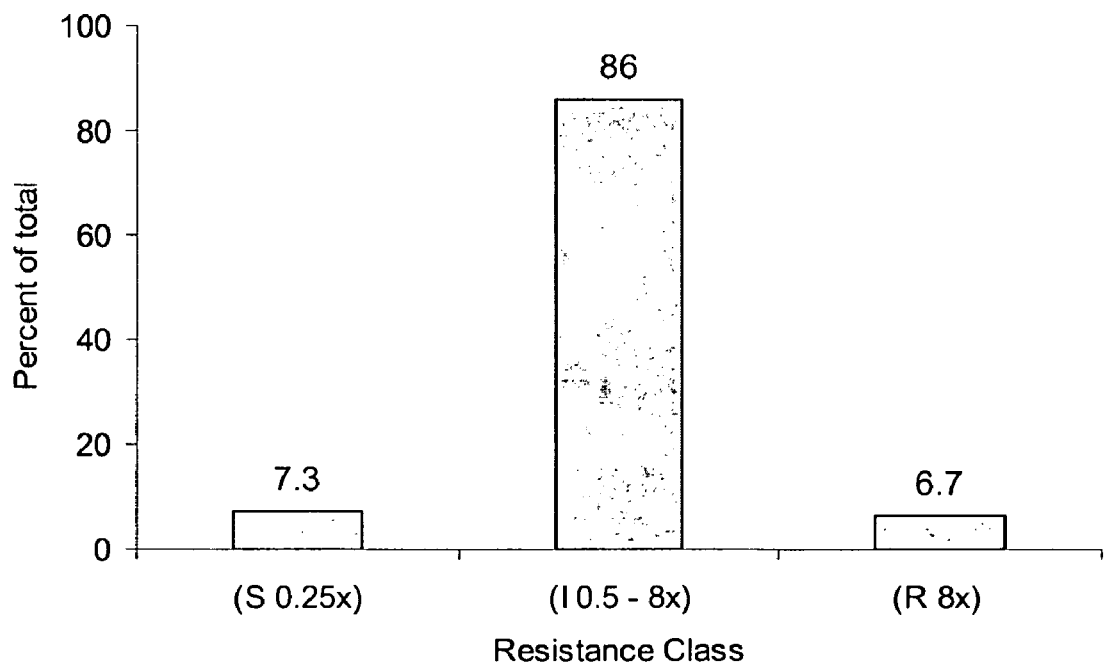
FIG. 5 is a graph illustrating the distribution of glyphosate resistant classes in a single $F_2bc_1$ population of 371 plants derived from a backcross between a glyphosate resistant $F_2$ hybrid plant with a sensitive perennial ryegrass.

Backcrossing between the resistant plants from F2 to the sensitive parent of perennial ryegrass is designed to re-capture agronomic characteristics of sensitive parents (perennial ryegrass). The level of glyphosate resistance in the F1bc1 population appears to be similar to the previous results in F1 population. Distribution of glyphosate sensitivity level in the F2bc1 population is illustrated in FIG. 5. A sample of the resistant plants from the F2bc1 is evaluated for the level of sensitivity at 0, 1, 2, 4, 6, 8, 10, 12, and 14× glyphosate and data is illustrated in FIG. 6. No injury is observed up to 6× glyphosate, slight injury is observed at 8× and 10×, and severe injury is observed at 12× glyphosate. The growth and development, including inflorescence of the resistant R clones from F2bc1 treated with glyphosate up to 8× is similar to the control plants.

Example 8

The level of glyphosate resistance is assayed from resistant rigid ryegrass EPSPS-expressing *Agrobacterium* that are transformed with a DNA construct encoding the resistant EPSPS enzyme (SEQ. ID. NO. 16).

An EPSPS gene (SEQ. ID. NO. 15) is obtained from glyphosate resistant rigid ryegrass. The EPSPS gene is ligated with the binary vector pFGC5941, a 11406 bp construct with kanamycin resistant gene, BAR gene as a selectable marker, and 35S Promoter. The ligation is cloned in pGEM vector and grown in LB broth. The plasmid from cloned pGEM is confirmed for the inserted EPSPS gene by PCR.

The confirmed plasmid is transformed into *Agrobacterium tumefaciens* by "freeze thaw technique" using liquid nitrogen. The transformed *Agrobacterium* is grown in LB plated and maintained 28° C. for 72 h. Some colonies are grown in LB broth for 24 h and tested for the inserted EPSPS gene by PCR. The confirmed *Agrobacterium* is grown in 50 mL LB broth for 24 h. The *Agrobacterium* is centrifuged at 5000×g for 10 min, and the pellets are diluted with 2 mL 1.0 M $CaCl_2$. At the same time, a wild-type *Agrobacterium* is also grown and extracted similar to the transformed *Agrobacterium*. The *Agrobacterium* solutions (10 μL) are grown in 50 mL media containing 1×M-9 salt media (SIGMA), 20 mM glucose, 2 mM $MgSO_4$, and glyphosate at 0, 0.25, 0.5, 0.75, 1.0, 1.5, and 2 mM.

The growth (indicated by Optical Density 600 nm) is measured after 48 hours. Results are shown in Table 6 and FIG. 7.

TABLE 6

Growth of wild-type and transformed Agrobacterium in M-9 media with various glyphosate concentrations.

| Glyphosate | Wild-type Agrobacterium | | Transformed Agrobacterium | |
|---|---|---|---|---|
| mM | OD 600 nm | Percent | OD 600 nm | Percent |
| 0.00 | 0.638 | 99 | 0.64 | 100 |
| 0.25 | 0.236 | 37 | 0.632 | 98 |
| 0.50 | 0.005 | 0.8 | 0.185 | 29 |
| 0.75 | 0.005 | 0.8 | 0.097 | 15 |
| 1.00 | 0.004 | 0.8 | 0.025 | 4 |
| 1.50 | 0.004 | 0.8 | 0.024 | 4 |
| 2.00 | 0.004 | 0.8 | 0.02 | 3 |

Embodiments and the examples described herein are exemplary and not intended to be limiting in describing the full scope of compositions and methods of this disclosure. Equivalent changes, modifications and variations of some embodiments, materials, compositions and methods can be made within the scope of the present disclosure, with substantially similar results.

What is claimed is:

1. The germplasm deposited under American Type Cultural Collection as Penner Ryegrass (PTA-8157 deposited on Jan. 19, 2007).

2. A method of obtaining a cultivated field that is substantially free of a weed variety to which said field is susceptible, the method comprising:
   providing a cultivated field comprising a glyphosate resistant grass of economic value, wherein said glyphosate resistant grass of economic value is not created by a genetic transformation and comprises
   germplasm deposited under American Type Cultural Collection as Penner Ryegrass (PTA-8157 deposited on Jan. 19, 2007); and
   applying to said cultivated field a herbicidally effective amount of a mixture comprising glyphosate.

3. The method according to claim 2, wherein said providing comprises planting seed capable of growing said glyphosate resistant grass of economic value.

4. The method according to claim 2, wherein said glyphosate resistant grass of economic value comprises germplasm from a non-transgenic glyphosate resistant *Lolium rigidum*.

5. The method according to claim 2, wherein said glyphosate resistant grass of economic value is a turfgrass selected from the group consisting of ryegrass, fescue, combinations thereof, and hybrids thereof.

6. The method according to claim 2, wherein said cultivated field is a lawn.

7. The method according to claim 6, wherein said lawn is selected from a group consisting of a golf course fairway, a golf course rough, a golf course tee box, a lawn, an athletic field, a park, a school yard, a roadside, a right of way, a trail, or a sod.

8. The method according to claim 2, wherein said glyphosate resistant grass of economic value is naturally bred.

9. The method according to claim 2, wherein said weed variety is selected from the group consisting of a dandelion, goosegrass, ground ivy, clover, crabgrass, thistle, plantain, knotweed, quackgrass, nimble weed, tall fescue, creeping bent grass, zoysiagrass, Bermudagrass, Dallisgrass, bindweed, black medic, carpetweed, chickenweed, creeping beggarweed, cudweed, curly dock, English daisy, evening primrose, false dandelion, filaree, Florida pusley, henbit, lambsquarters, mallow, oxalis, pennywort, pigweed, prickly lettuce, purslane, ragweed, sheep sorrel, Shepardspurse, sowthistle, speedwell, spotted spurge, tansy ragwort, wild carrot, wild geranium, wild morning-glory, wild onion, wild violet, foxtail, Johnsongrass, nutsedge, bahiagrass, barnyardgrass, poa annua, sandbur, and combinations thereof.

10. The method according to claim 2, wherein said cultivated field is substantially free of weeds.

11. The method according to claim 2, wherein said glyphosate resistant grass of economic value is a perennial glyphosate resistant turf grass.

* * * * *

UNITED STATES PATENT AND TRADEMARK OFFICE
CERTIFICATE OF CORRECTION

PATENT NO. : 7,906,709 B2
APPLICATION NO. : 11/656817
DATED : March 15, 2011
INVENTOR(S) : Donald Penner and Marulak Simarmata It is certified that error appears in the above-identified patent and that said Letters Patent is hereby corrected as shown below:

Column 2, line 4, after "thereof", insert --.--.

Column 11, line 40, "$F_i$" should be --$F_1$--.

Column 13, line 61, "(2003)" should be --(2003))--.

Column 14, lines 4-5, "nucleic acid molecule nucleic acid molecule" should be --nucleic acid molecule. Nucleic acid molecule--.

Column 20, line 15, "(1985)" should be --(1985))--.

Column 25, line 48, "F2" should be --$F_2$--.

Column 28, line 29, "5µl" should be --5 µl--.

Column 28, line 39, "FAM®" should be --FAM™--.

Signed and Sealed this
Twenty-second Day of November, 2011

David J. Kappos
*Director of the United States Patent and Trademark Office*